(12) United States Patent
Liepold et al.

(10) Patent No.: US 7,766,029 B2
(45) Date of Patent: Aug. 3, 2010

(54) VALVE

(75) Inventors: Gerhard Liepold, Watchung, NJ (US);
Dietrich Bizer, Madison, NJ (US)

(73) Assignee: GL Tool & Manufacturing Company, Inc., Livingston, NJ (US)

( * ) Notice: Subject to any disclaimer, the term of this patent is extended or adjusted under 35 U.S.C. 154(b) by 814 days.

(21) Appl. No.: 11/658,779

(22) PCT Filed: Feb. 1, 2005

(86) PCT No.: PCT/US2005/002909

§ 371 (c)(1),
(2), (4) Date: Jan. 29, 2007

(87) PCT Pub. No.: WO2006/022816

PCT Pub. Date: Mar. 2, 2006

(65) Prior Publication Data

US 2009/0194168 A1    Aug. 6, 2009

Related U.S. Application Data

(60) Provisional application No. 60/592,698, filed on Jul. 30, 2004.

(51) Int. Cl.
*F16K 17/40* (2006.01)
(52) U.S. Cl. ..................... 137/68.3; 251/266
(58) Field of Classification Search ................. 251/162, 251/172, 252, 266; 137/553, 67, 68.11–68.3
See application file for complete search history.

(56) References Cited

U.S. PATENT DOCUMENTS 293,515 A * 2/1884 Porsch, Jr. ................. 251/225

328,529 A * 10/1885 Singer ........................ 239/435
1,064,376 A * 6/1913 Race .......................... 251/252

(Continued)

FOREIGN PATENT DOCUMENTS

AT            6 052 U        3/2003

(Continued)

*Primary Examiner*—John Rivell
*Assistant Examiner*—Macade Brown
(74) *Attorney, Agent, or Firm*—Hoffman & Baron, LLP

(57) ABSTRACT

A re-closable valve (1, 100, 700, 800) for use in sterile fluid transfer has a body (5) with open entry and exit sides (2, 3) and a passageway (4) for fluid therebetween. The entry side is connectable to an opening of a separate vessel and the exit side is connectable to downstream processing. The entry side includes a first rupturable seal (5b, 500) blocking the opening of the entry side. A piston (9) is connected to an actuator (7) via a cam mechanism (8, 85, 10) which moves the piston (9) axially in the passageway (4) and to the first seal (5b, 500). On movement of the piston (9) during a first actuation, the first seal (5b, 500) is torn free from the entry side to open the valve for fluid transfer. A sharp rim (15) surrounds the opening of the entry side and a curved surface area (193) encircles the piston exterior proximal the entry side. The valve (1, 100, 700, 800) can be re-closed by moving the piston (9) during a subsequent actuation thus engaging the sharp rim (15) with the curved surface area (193) which plastically deform to from a second seal. Arrangements are included to enable the valve (1, 100, 700, 800) to be multiply re-opened and re-closed, if desired.

32 Claims, 17 Drawing Sheets

U.S. PATENT DOCUMENTS

| | | | |
|---|---|---|---|
| 1,111,390 A * | 9/1914 | Kelly | 251/221 |
| 2,642,256 A * | 6/1953 | Stehlin | 251/252 |
| 3,397,712 A * | 8/1968 | Boroson | 137/68.27 |
| 3,623,495 A * | 11/1971 | Erb | 137/69 |
| 3,750,959 A * | 8/1973 | Weikert | 239/539 |
| 4,544,132 A * | 10/1985 | Allen et al. | 251/318 |
| 6,193,108 B1 * | 2/2001 | Lepsius et al. | 222/83 |
| 6,354,466 B1 | 3/2002 | Karpisek | |
| 2002/0170922 A1 * | 11/2002 | Anderson | 222/83 |
| 2004/0195535 A1 | 10/2004 | Garnreiter et al. | |
| 2005/0150546 A1 * | 7/2005 | Liepold et al. | 137/68.3 |

FOREIGN PATENT DOCUMENTS

| | | |
|---|---|---|
| WO | WO03/038322 | 5/2003 |
| WO | WO03/090842 | 11/2003 |

* cited by examiner

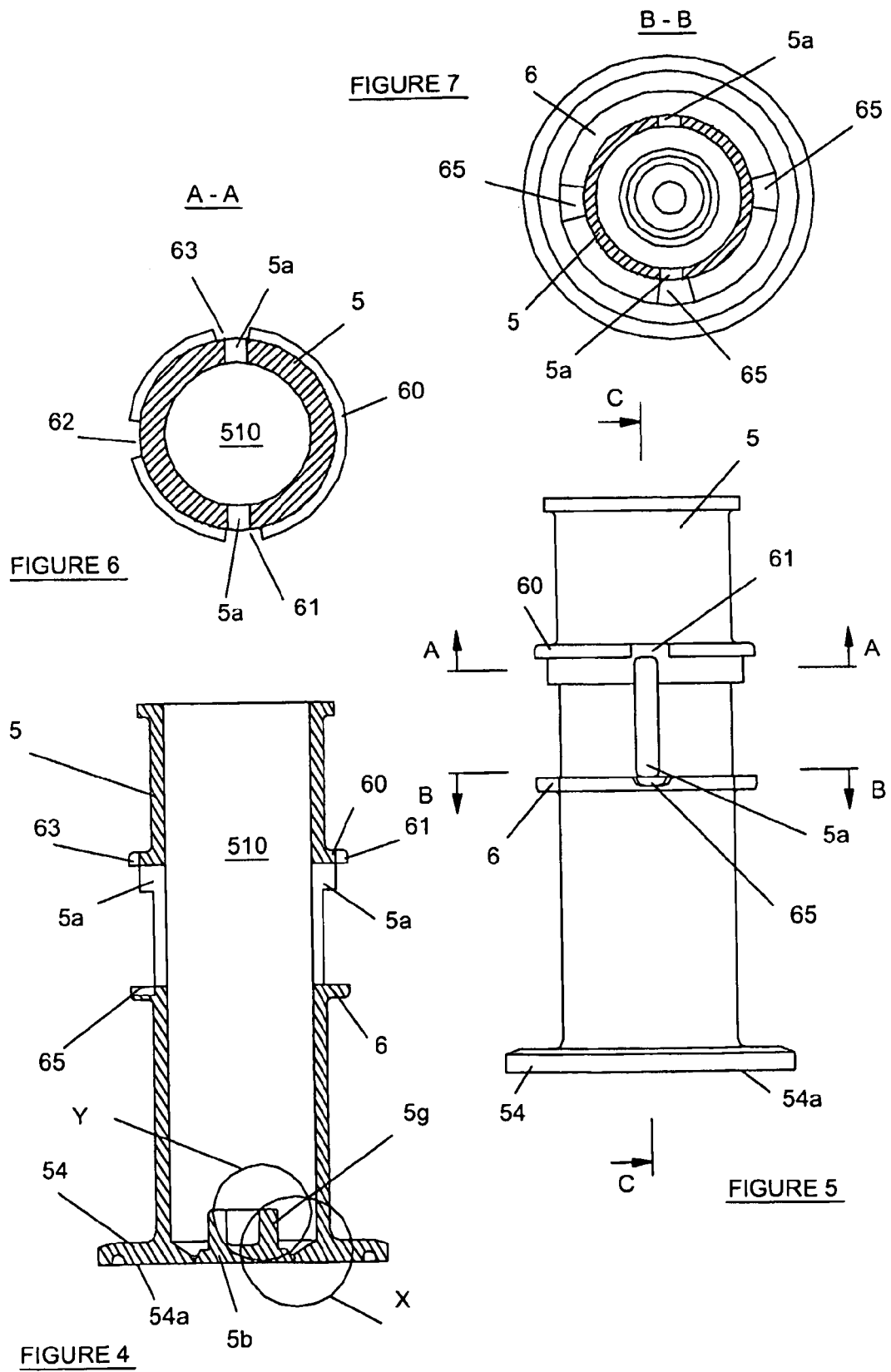

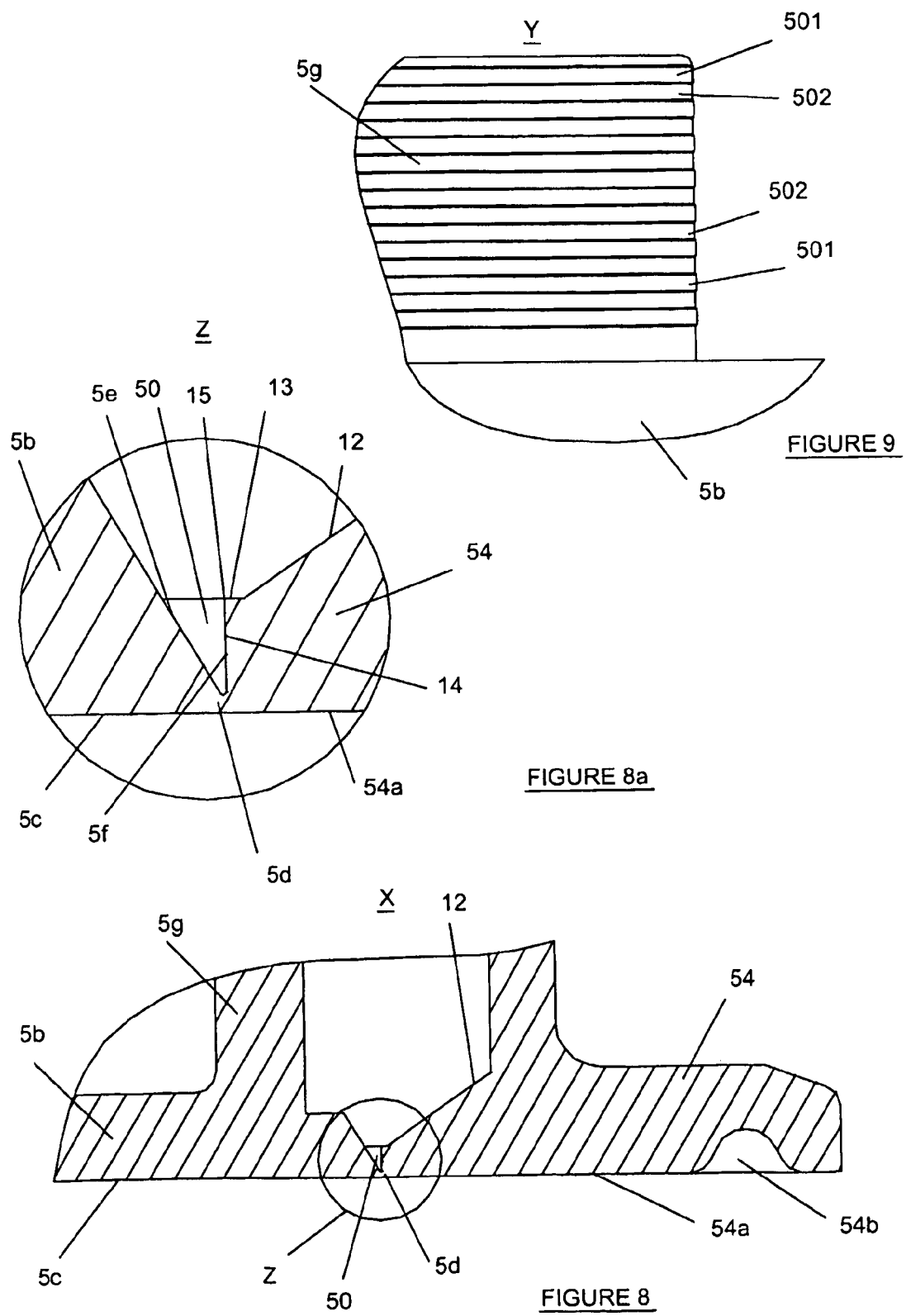

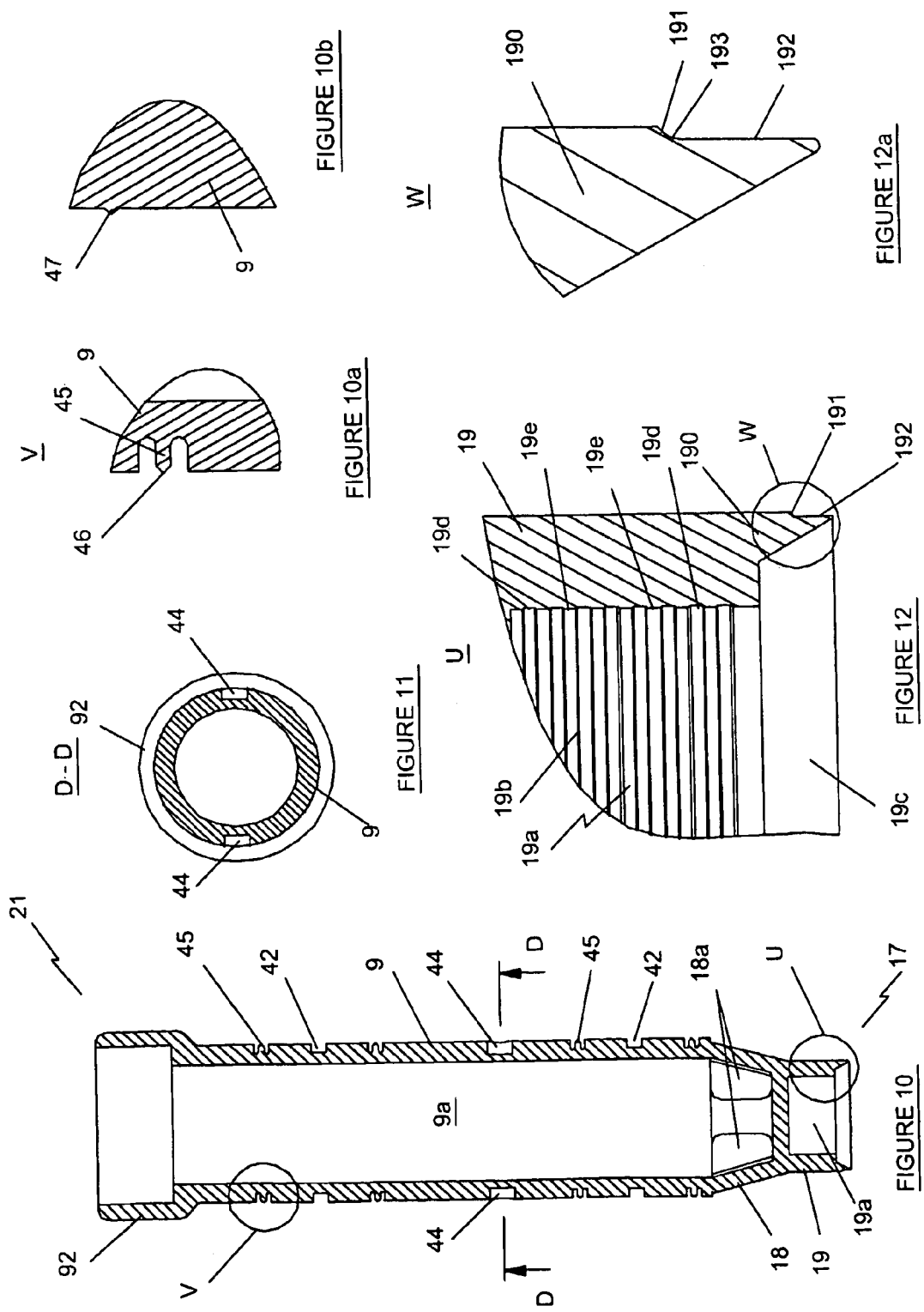

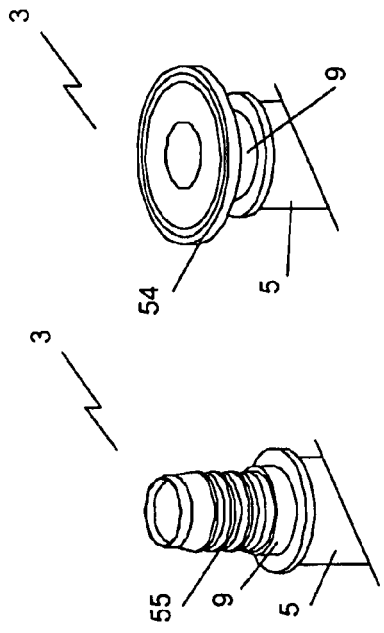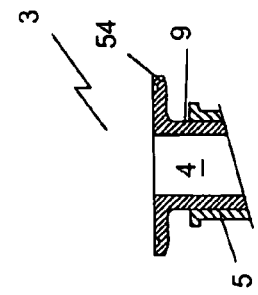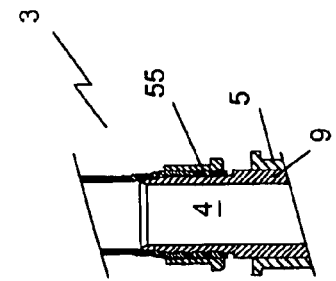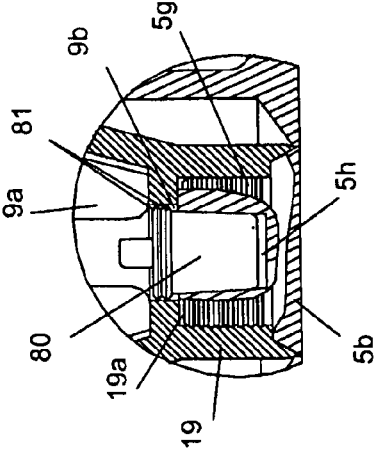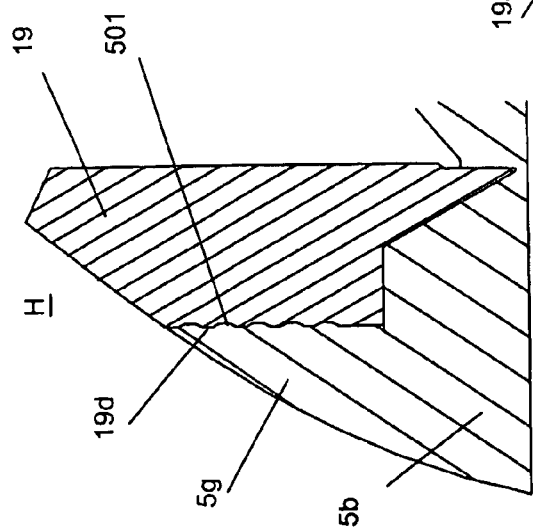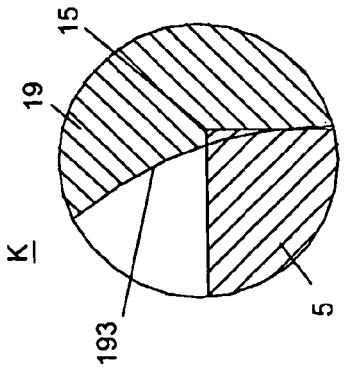

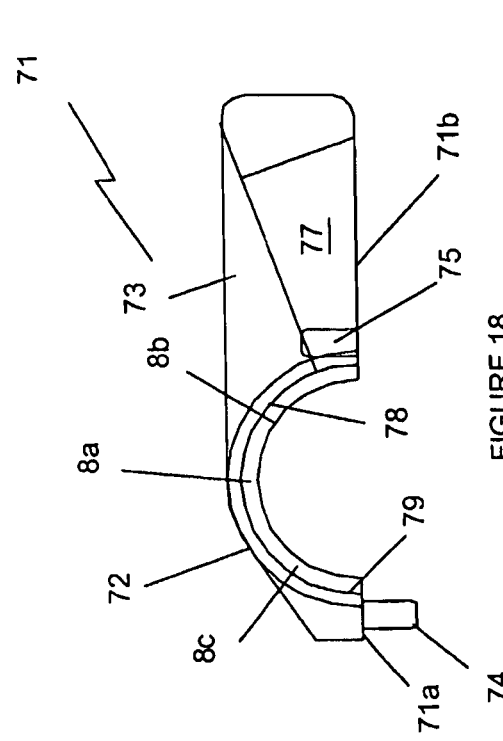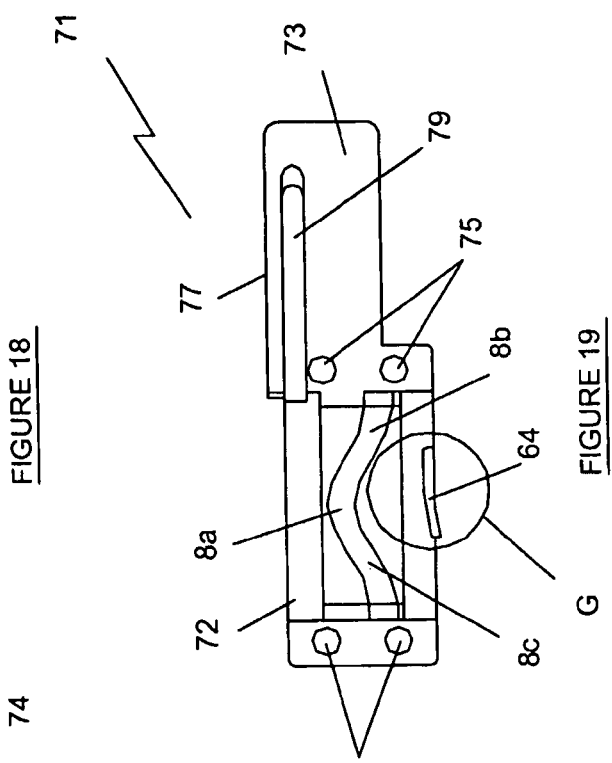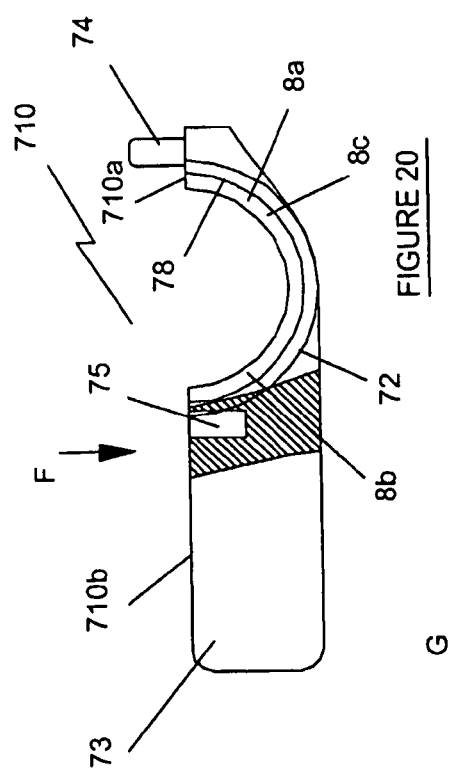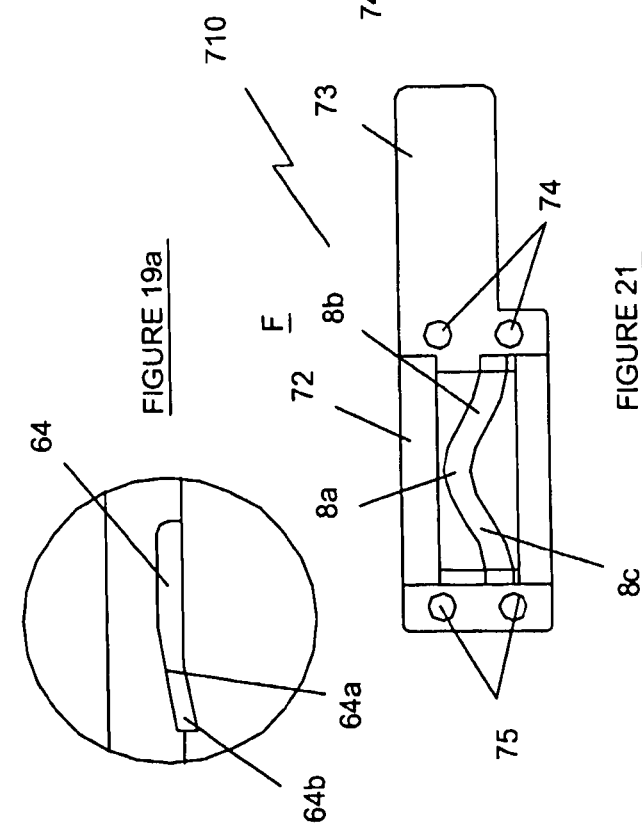

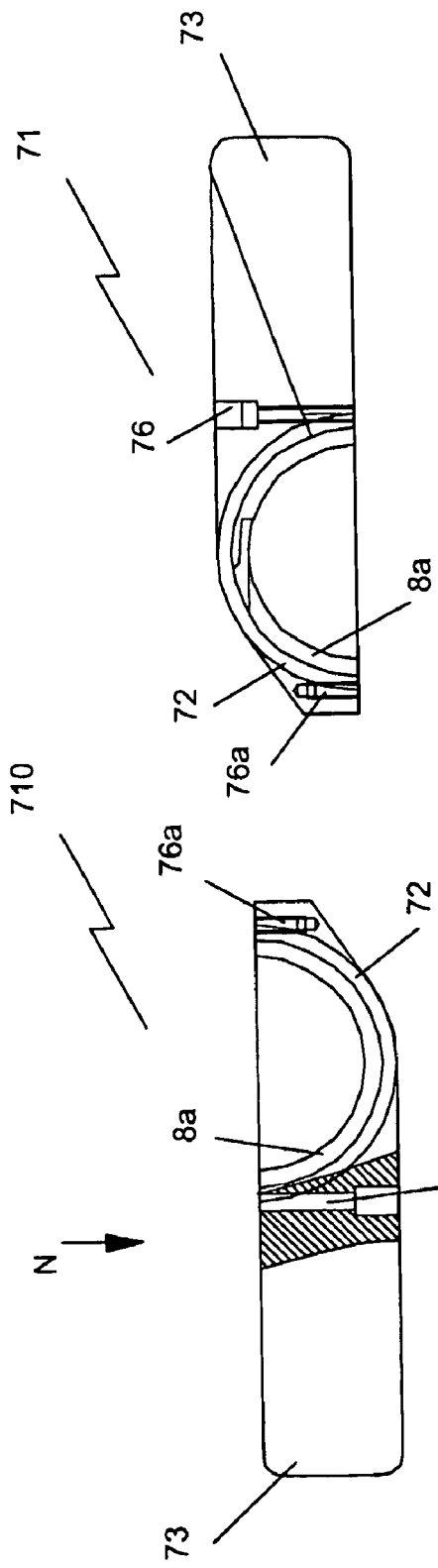
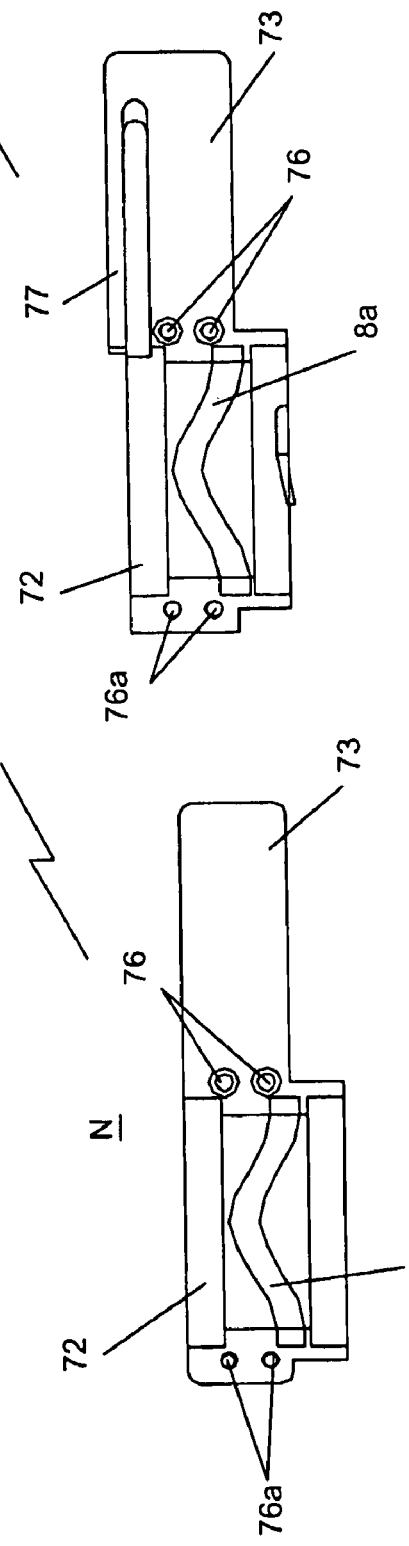
FIGURE 22
FIGURE 23
FIGURE 24
FIGURE 25

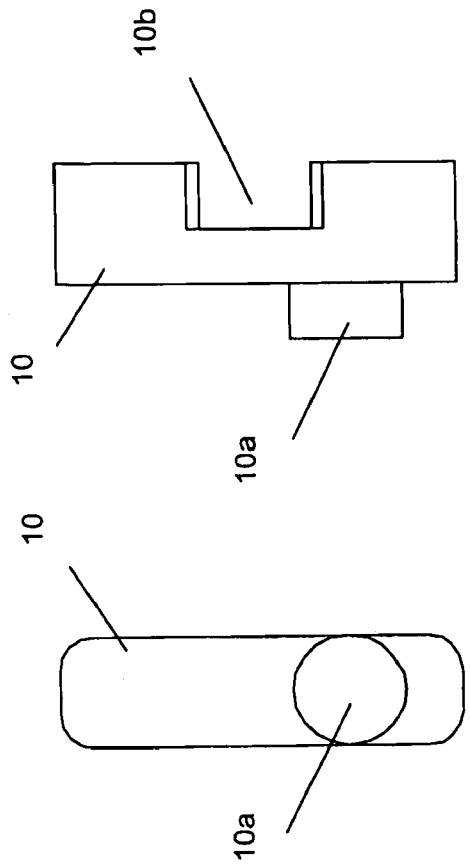
FIGURE 28
FIGURE 29
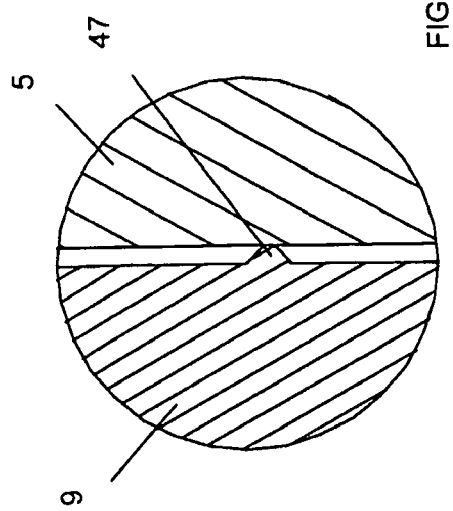
FIGURE 27
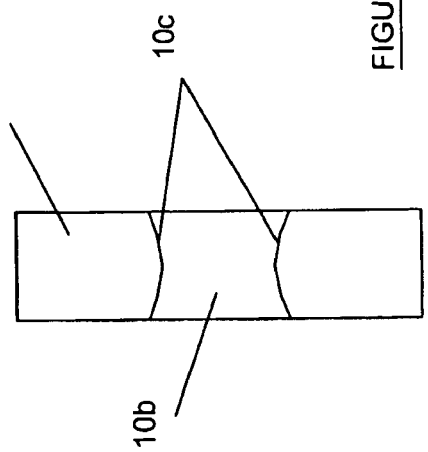
FIGURE 30
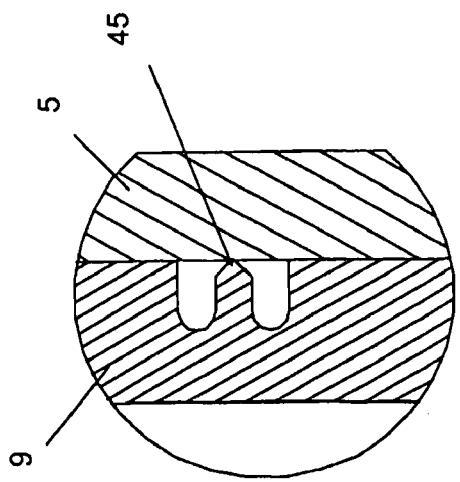
FIGURE 26

VALVE

CROSS-REFERENCE TO RELATED APPLICATIONS

This application is the National Stage of International Application No. PCT/US2005/002909, filed Feb. 1, 2005, which claims the benefit International Application No. PCT/US2004/024732, filed Jul. 30, 2004, and also claims the benefit of U.S. Provisional Application No. 60/592,698, filed Jul. 30, 2004, the contents of which are incorporated by reference herein.

FIELD OF THE INVENTION

The present invention relates to a valve apparatus and in particular to a valve apparatus useful in systems for the sterile transfer of fluids.

BACKGROUND OF THE INVENTION

Validation and accountability are vital in most scientific industries and especially so in the pharmaceutical and biotechnological industries. A major challenge to these industries is the need to demonstrate accurately and reproducibly that sterility is achieved and maintained throughout production lines within a plant. This must be done in a manner which meets the stringent requirements of regulatory bodies such as the United States FDA. Acceptable standards can be difficult to be met when a substance is transferred from one sterile location to another sterile location by non direct means.

One current practice includes providing a holding vessel into which substance can be transferred by means of a connecting valve. The holding vessel is transferred to the second sterile location and the substance is then transferred from the holding vessel into the second sterile location via one or more connecting valves. The connecting valves and holding vessel can be sterilised using conventional techniques such as gas, radiation or steam sterilisation. However during connection of the connecting valve to the first sterile location, the external connecting surface of the connecting valve is exposed to the atmosphere and sterility of the valve is compromised.

Alternative methods of substance transfer suffer from similar problems.

For example, in the use of an autoclavable port, where a non-sterile male port is attached to an empty non-sterile bulk vessel prior to sterilization, the entire assembled apparatus is then sterilised by autoclaving. However, a major disadvantage of this technique is that the vessel must be empty before sterilisation.

Alternatively, an irradiated port can be used, where a non-sterile male port is attached to an empty non-sterile disposable bag prior to sterilisation of the whole by irradiation. Again a major disadvantage associated with this system is that the bag must be empty before sterilisation.

A further method of substance transfer involves connecting a transfer port to a vessel under aseptic conditions. With this method it is irrelevant whether or not the vessel is empty or filled. However despite the necessity to undertake these actions in a designated 'Grade A' zone, there is an increased risk of contamination due to the making and breaking of various connections. The mere fact that a 'Grade A' zone is required to complete these actions requires a significant financial investment by a company wishing to employ this technique.

Another technique incorporates the use of a tube fuser. A sterile bulk vessel is attached to tubing emanating from a sterile port through a tube fuser. This technique is undesirable for numerous reasons including the restricted choice of tubing. This in turn limits the types of substance that can be transferred through the tubing. It is also undesirable to use wetted tubing. Furthermore there is also a potential risk of cross-contamination and re-contamination.

Despite the numerous attempts to find a sterile method of substance transfer none have been wholly successful. In all of the above techniques the sterility of the port or valve used to transfer the substance from one vessel to another is compromised during the connection process or is susceptible to contamination. This is undesirable and leads to problems when validating a product.

Piston-operated valves for the above applications are known. These act by moving a piston up and down or sliding over and back within an apertured housing so as to cover or uncover the fluid communication apertures of the housing. O-ring seals are provided for sealing between the open and closed valve positions. Such valves therefore have slots for receiving the O-rings and the difficulties of assuring that these slots and the spaces about them are not subject to contamination render them questionable for use in sterile transfer systems.

GB 1,573,482 discloses a rigid tubular member positioned within a flexible tube with one end of the tubular member being blocked by an integrally formed plug. A rigid shaft extends from the plug along the flexible tube and an area of weakness is defined between the plug and the tubular member. The plug is broken free from the tubular member by manually gripping the flexible tube from outside and pulling, bending or twisting the rigid shaft thus breaking it off the tubular member and opening the tubular member for fluid transfer. The opened end can be closed again by sealingly re-inserting the plug into it.

AT 006,052 U1 describes a valve having a hollow housing with two open ends and a piston movable within the housing. A deformable O-ring is disposed around an end portion of the piston which blocks one of the open ends of the housing, the O-ring providing a seal between the end portion of the piston and the opening. The piston is connected to the housing via a screw thread so that rotation of the housing about the piston causes the piston to move away from the opening to open the valve. Reverse rotation of the housing re-closes the valve.

WO 03/090,842 provides a piston-operated valve having an elongate open-ended housing in which one of the ends is blocked with a "tear-away" seal formed continuously with the housing. On operation of an actuator, the piston moves within the housing and breaks the seal thus opening the valve for passage of fluid. The broken-away seal is retained in a deployed position away from the open end of the valve. This valve cannot be re-closed after the seal has been broken and therefore there exists a risk of contamination of the environment from e.g. biological material being transferred through the valve.

SUMMARY OF THE INVENTION

The present invention seeks to alleviate further the above-mentioned problems associated with the prior art valves.

Accordingly, the present invention provides a valve comprising a body having first and second open ends and a passageway for fluid between the ends, the first end including a coupling means for sealingly connecting the body about an opening of an external device and a first seal formed with the coupling means closing the open area of the first end, which in use is placeable in register with the opening of the external device, the valve further including a seal displacement means movable within the body so as to displace the first seal permitting fluid to pass along the passageway between the ends, the coupling means and the first seal presenting an external sterilisable mating surface for sealingly mating with a mating surface about the opening in the external device, and an actuation means for moving the displacement means in a first actuation between a ready state in which the first seal is intact and the valve is closed and an open state in which the first seal is separated from the coupling means and moved with the displacement means away from the mating surface so that the valve is open for passage of fluid, the actuation means being engaged with the displacement means via a connecting means and with the body, the connecting means enabling the displacement means to move linearly and non-rotationally along a straight path within the body without side deflection from said straight path;

and wherein the displacement means includes a first plastically deformable portion encircling an outer surface of a member of the displacement means and the coupling means includes a second plastically deformable portion encircling its open area which becomes exposed when the first seal is separated therefrom, the displacement means being movable in a second subsequent actuation to bring the first and second plastically deformable portions into engagement so as to form a second seal between said first and second portions, the displacement means comprising a face continuous with the first portion so that the second seal and the face close the fluid passage.

Advantageously, a mutually engageable gripping means is provided on the first seal and on the displacement means enabling the displacement means to move the first seal away from the mating surface by stamping the first seal outwardly or withdrawing the first seal into the body of the valve.

In one embodiment, the continuous face comprises a portion of the outer surface of the displacement means facing the opening of the first end of the valve and the outer face of the first seal wherein said portion and the first seal are sealingly coupled together. In another embodiment the continuous face may comprise a face on the displacement means facing the opening of the first end of the valve.

In a most preferred embodiment the displacement means is so engaged with the actuation means via the connecting means that during third and subsequent alternating actuations the first and second plastically deformable portions alternately separate and engage again in order to re-open or re-close the valve. These multiple actuations can be performed as many times as required for any possible reason.

In a most preferred embodiment, the displacement means is engaged with the actuation means via a connection means so that during the first actuation the connection means causes the displacement means to move within the body in a direction towards the second end of the valve, and the first seal is withdrawn into the interior of the body; and during the second subsequent actuation the connection means causes the displacement means to move in the reverse direction towards the first end of the valve to engage the first and the second plastically deformable portions and form the second seal.

In another embodiment, the displacement means is engaged with the actuation means via a connection means so that during the first actuation the connection means causes the displacement means to move within the body in a direction towards the first end of the valve, and the first seal is pushed outwardly form the opening of the first end of the valve into a passageway of a separate vessel; and during the second subsequent actuation the connection means causes the displacement means to move further in the same direction to engage the first and the second plastically deformable portions and form the second seal.

The first seal is most preferably formed integrally with the coupling means, and ideally an endless weakened junction region is provided between the coupling means and the first seal, said junction region enclosing the seal and said junction region comprising at least one fracture line so that when the displacement means moves on first actuation to open the valve it ruptures the junction region along the at least one fracture line thus separating the first seal from the coupling means and opening the valve for passage of fluid.

In a preferred embodiment, the junction region is formed by way of reduction of material thickness between the first seal and the coupling means. Most preferably, the reduction in thickness is obtained by forming a notch between the first seal and the coupling means wherein the notch is defined by a pair of converging surfaces, one of which belongs to the first seal and the other of which belongs to the coupling means and wherein the line of intersection of said surfaces defines the fracture line of the weakened junction region. In a most preferred arrangement, the notch is formed on those surfaces of the first seal and the coupling means which in use face the interior of the body of the valve. Preferably, the converging surface of the coupling means is substantially parallel to a longitudinal axis extending between the ends of the valve. This enables a portion of the displacement means comprising the first plastically deformable portion to occupy wholly the opening of the coupling means upon engagement of the first and second portions. The junction region ideally has a substantially uniform cross-section along the entire length thereof.

The provision of a junction region having uniform cross-section and a fracture line formed by intersection of a pair of converging surfaces enables quicker and easier separation of the first seal from the coupling means. Also, such a fracture line yields neat and clean fracture surfaces upon separation of the first seal from the coupling means thus reducing the risk of loose particles of the material contaminating the fluid flowing through the valve.

Ideally, one of the first and the second plastically deformable portions has an endless encircling sharp rim and the other plastically deformable portion has an endless encircling curved surface area so that when the displacement means is moved to close the valve, the sharp rim engages the curved surface area and displaces a portion of the curved surface area thereby deforming the materials of the sharp rim and the curved surface area to form the second seal at the opening of the valve. The contact between the sharp rim and the curved surface is sufficiently close and tight to form the second seal which prevents fluid from passing to from the valve.

It will be appreciated that the first and the second plastically deformable portions may be provided as attachments releasably couplable with the seal displacement means and the body, respectively. These portions may be made from a material different from those of the body and the displacement means as long as they are plastically deformable to enable formation of the second seal and can withstand sterilisation. It is essential that no lasting plastic deformation of the material of the first and the second portions occurs during sterilisation, and the first and second portions remain within a predetermined range of dimensions to ensure effective sealing, otherwise the integrity of the second seal may be compromised.

Preferably, the body of the valve, the first seal and the seal displacement means are manufactured from a plastic material. It will be appreciated that other materials may be used for manufacture of the body, the first seal and the seal displacement means. Such other materials may include metal, ceramic or any other material found suitable to withstand rigours of sterilisation process.

Ideally, the first plastically deformable portion is integrally formed with the member of the displacement means, the member being disposed proximal the first open end of the valve in use and comprising the curved surface area; and the second plastically deformable portion is integrally formed with the coupling means and comprises the sharp rim.

In a most preferred arrangement, in the ready state of the valve, the first and second plastically deformable portions are axially separated along a longitudinal axis of the valve extending between the ends of the valve and the displacement means is engaged with the actuation means via the connecting means so that the distance travelled by the displacement means on the second actuation is sufficient to bring said portions into engagement to form the second seal. The linear, non-rotational motion of the displacement means with no side deflection from a straight path within the body of the valve ensures integrity of the second seal.

In a preferred embodiment, the gripping means comprise a snap-fit arrangement between the first seal and the seal displacement means, comprising first and second snap fit members provided on the first seal and the seal displacement means, respectively.

Ideally, the first snap-fit member comprises a wall upstanding from the inner facing side of the first seal, the wall having a series of alternating ribs and grooves encircling an outer surface thereof, and the second snap-fit member is provided in a recess formed in a portion of the displacement means proximal the first seal in use, the recess being configured for receiving the wall, the surface of the portion of the displacement means which defines the recess comprising a series of alternating ribs and grooves which match those of the wall and encircle said surface, so that on assembly of the valve, when the wall is received in the recess, the ribs of the wall and in the recess first resiliently deform allowing the wall to enter the recess, and then snap into respective grooves of the wall and the recess to couple the first seal with the seal displacement means.

Preferably, the displacement means comprises a piston having an internal bore which defines a portion of the fluid passageway of the valve, the piston having a first end which is open and a second end, the member comprising the curved surface area being provided at the second end of the piston; the piston further comprising one or more apertures provided in a wall of the piston adjacent the second end of the piston so that fluid may pass between the interior of the piston and the first end of the valve via the or each aperture.

In one arrangement, a portion of the coupling means surrounding the first seal may be provided as an attachment which includes the first seal and the coupling means. The attachment is secured to the body of the valve at the first end of the valve and is fixed in place by suitable means such as, for example, screws, snap-fit coupling etc. The body and the attachment are so configured that the contact between the body and the attachment is fluid-tight. A new attachment with an unbroken seal is then placed into the position blocking the open first end of the valve. Another modification of such an attachment may be formed and shaped to provide a secondary function of a sealing washer between the valve and the vessel to which it is coupled when the valve and vessel are secured together. In such a modification the first seal is ideally formed integrally with the washer, and when the washer is placed between the vessel and the valve, the seal blocks the open end of the valve. The seal of the washer is ideally coupled with the piston of the valve so that on movement of the piston within the valve the seal is separated from the washer to open the valve. In valve arrangements where an attachable seal is used, the housing of the valve can be made from hard materials such as stainless steel or ceramics which can withstand multiple sterilisations. If a stainless steel housing is used, then after each use the attachment can be removed and the housing can be re-sterilised and used again.

Ideally, the actuation means comprises a hollow actuator body movably mounted on the exterior of the valve body, the actuator body being connected to the piston via a cam pair to translate movement of the actuator in relation to the valve body into movement of the piston within the valve body, said cam pair cooperating with a guide means to enable the linear non-rotational motion of the piston along a straight path in the fluid passageway of the valve body so that no side deflection of the piston occurs during said motion.

In a most preferred arrangement, the cam has a first region for moving the first seal away from the position blocking the opening of the valve, a second region for displacing the piston in order to engage the first and second portions to form the second seal.

Ideally, the valve body and the actuator are cylindrical and the actuator is rotatably mounted on the cylindrical exterior of the body, the cam being endless and encircling the internal surface of the actuator and wherein a return region connects a start end of the first cam region and a terminal end of the second cam region to enable multiple revolutions of the actuator about the housing for repeated re-opening and re-closing of the valve.

It will be appreciated that other cam pairs may be provided for translation of movement of the actuator about the housing into linear motion of the piston. Most preferably, a pair of cam followers are disposed at opposing locations on the external surface of the piston.

Most preferably, the actuation means includes the actuation means includes a releasable safety lock means for preventing undesired movement of the seal displacement means and a handle by operation of which a user moves the actuator relative to the body, and the safety lock means comprises a tongue releasably engageable with the body for preventing movement of the actuator, the tongue being releasably engagable with the body upon completion of each actuation.

In another embodiment, the valve according to the invention may be activated by a sliding actuator. Such a sliding actuator has a pair of opposing parallel side walls, at least one wall having a cam extending along the wall. The actuator is mounted on the exterior of the housing and is slidably movable laterally perpendicular to the longitudinal axis of the body of the valve. The cam of the actuator is engaged with at least one cam follower. similar to that described above so that the sliding motion of the actuator in relation to the housing is translated to the piston via the cam pair and results in linear longitudinal motion of the piston within the housing.

Ideally, the valve has a stop means for preventing the actuator from moving in a reverse direction about the housing after completion of any actuation. This has the advantage that the first seal may not inadvertently or mischievously be returned to a position in which it appears to block the opening of the first end, which would be undesirable given that the integrity of the seal has been irretrievably lost by the first actuation which displaced the first seal.

Conveniently, the valve has at least one third seal for sealing between the body and the displacement means, the third seal comprising at least one deformable plastics rib formed on the body or on the displacement means for contacting the other of the body or the displacement means and for sealing between them when they are stationary or moving relative to one another. Ideally, the rib is formed integrally with the body or the displacement means. The rib is ideally sufficiently deformable and flexible so that it drags or wipes along the surface with which it is in contact as the body or the displacement means slide with respect to one another. In a preferred arrangement, a plurality of ribs are provided, axially spaced apart from one another along the path of relative movement between the body and the displacement means. Ideally, at least one rib formed intermediate the connecting means and the first end and at least one rib formed between the connecting means and the second end.

The valve of the invention is usable as a single-use valve which is discarded on completion of the fluid transfer following the first actuation. The second seal arrangement allows the valve to be re-closed after the first seal has been broken free from the coupling means. Re-closure may be required when, for example, after the first actuation of the valve a leak occurs at any location in the fluid transfer line or in any other hazardous circumstances. Re-closure is also a desirable feature where the valve has been used in a process of handling hazardous materials. Such materials will contaminate the interior of the valve and could also contaminate the outside environment upon dismantling of the apparatus were it not possible to re-close the valve. A valve intended for single-use is ideally manufactured from plastics material. Such a single-use valve has an advantage that costly operations such as cleaning, storage, testing and validation are excluded from the technological process. Also, a single-use disposable valve reduces the risk of cross-contamination.

The present valve may be either a fixed length valve in which the travel of the piston occurs within the housing, or a variable length one in which the piston projects outwardly as the first seal is withdrawn into the interior of the housing.

The above described arrangement may be modified so that first and second seals close each of the first and second open ends of the body, the second end of the valve including a second coupling means having a first seal formed therewith, each first seal being movable by a separate displacement means axially spaced apart from each other within the body and wherein each displacement means includes a first plastically deformable portion and each coupling means includes a second plastically deformable portion so that both ends of the valve can be opened and/or closed. In one arrangement, each displacement means is connected to a separate actuation means to enable independent opening and closing of the valve ends. In another arrangement, each displacement means is connected to the same actuation means enabling an operator to change the state of the valve with a single actuation.

In yet another arrangement, the valve comprises a pair of bodies each having first and second open ends, the bodies being coupled to each other at the second ends so that the passageway of the valve extends between the opposing first ends of the pair of bodies and wherein first and second seals close the first open ends of the bodies, each first seal being movable by a separate displacement means disposed in its respective body and wherein each displacement means includes a first plastically deformable portion and a second plastically deformable portion surrounds the openings of the coupling means at each of the first ends so that the first ends of the valve can be opened and/or closed.

Such a "double-ended" valve may be either a fixed length valve in which the travel of the displacement means occurs within the valve body, or a variable length in which portions of the displacement means project outwardly as the first seals are separated from the coupling means. A fixed length valve is useful for connecting rigid pipes or vessels having fixed length between their openings. A variable length valve is suitable for connecting openings of flexible tubing, or indeed an opening of a rigid pipe and an opening of a flexible tube.

In another aspect the invention provides a process for the sterile transfer of fluid from a first vessel to a second vessel comprising the steps of:
a) coupling a first valve and a second valve to respective open ends of a length of a conduit;
b) placing the conduit with the valves attached in a bag and sterilising the bag and its contents;
c) opening the bag and removing the valve/conduit assembly thereby exposing the external sealing surfaces of the valves to environmental contamination;
d) coupling the first valve to a first vessel and sterilising the interior of the first vessel thereby also resterilising the exposed face of the first valve;
e) transferring the first vessel with the attached valve/conduit assembly to the site of a second vessel;
f) coupling the second valve to the second vessel and sterilising the interior of the second vessel thereby also resterilising the exposed face of the second valve; and
g) opening the valves thereby breaking the first seal of each valve and allowing fluid to flow between the first and second vessels;
h) re-closing each valve by deploying the actuating means to close the second seals;
i) sanitising the interiors of the first and second vessels together with the closed faces of the valves facing the vessels; and
j) de-coupling the valves from the vessels and discarding the valve/conduit assembly.

Of course, the process is not limited to transfer of fluid between two vessels and many different fluid sources, including pipes may be connected in the above described manner.

Ideally, the process includes effecting any desired number of closing and opening steps of either valve between steps g) and h).

It will be appreciated that the first and second vessels can reside at different locations or be in close proximity to each other. It will also be appreciated that instead of a pair of valves connected to a length of a conduit, a single "double-ended" valve as described above can be used.

Optionally, the valve may include a non-releasable lock for blocking the actuator on completion of the second actuation of the valve, providing a valve intended for a single use only.

BRIEF DESCRIPTION OF THE DRAWINGS

The invention will now be described with reference to the accompanying drawings which show by way of example only several embodiments of a valve in accordance with the invention. In the drawings:

FIG. 4 is a cross-sectional elevation of a housing of the valve according to the invention;

FIG. 5 is an elevation view of the housing of FIG. 4;

FIG. 6 is a cross-sectional plan view of the housing of FIG. 4 along the line A-A;

FIG. 7 is a cross-sectional plan view of the housing of FIG. 4 along the line B-B;

FIG. 8 is an enlarged view of area X of FIG. 4;

FIG. 8a is an enlarged view of area Z of FIG. 8;

FIG. 9 is an enlarged view of area Y of FIG. 4;

FIG. 10 is a cross-sectional elevation of a piston of the valve according to the invention;

FIG. 10a is an enlarged view of area V of FIG. 10 showing a side seal of the piston;

FIG. 10b is a modification of the side seal of FIG. 10a;

FIG. 11 is a cross-sectional plan view of the piston of FIG. 10 along the line D-D;

FIG. 12 is an enlarged view of area U of FIG. 10;

FIG. 12a is an enlarged view of area W of FIG. 12;

FIG. 13 is an enlarged view of area H of FIG. 2;

FIG. 13a shows a modification of a coupling arrangement between the seal and the piston;

FIG. 14 is an enlarged view of area K of FIG. 35 showing re-sealing surfaces of the valve according to the invention;

FIG. 15 is a perspective view of a first modification of a coupling at a second end of the valve of FIG. 1;

FIG. 15a is a cross-sectional elevation of the coupling of FIG. 15 coupled with a tubing end;

FIG. 16 is a perspective view of a second modification of the coupling at the second end of the valve of FIG. 1;

FIG. 16a is a cross-sectional elevation of the coupling of FIG. 16;

FIGS. 18 and 19 are plan and elevation views, respectively of one component half of a rotary actuator of the valve of FIG. 1;

FIG. 19a is an enlarged view of area G of FIG. 19;

FIG. 20 is a plan view of the other component half of a rotary actuator of the valve of FIG. 1;

FIG. 21 is an elevation of the component half of FIG. 20 as seen in the direction of arrow F in FIG. 20;

FIGS. 22 and 23 are plan and elevation views, respectively of one component half of a modification of the rotary actuator;

FIG. 24 is a plan view of the other component half of the modified rotary actuator;

FIG. 25 is an elevation of the component half of FIG. 24 as seen in the direction of arrow F in FIG. 20;

FIG. 26 is an enlarged view of area J of FIG. 2 showing the side seal of the piston engaged with the interior of the housing of the valve;

FIG. 27 shows the modification of the side seal engaged with the interior of the housing;

FIGS. 28 to 30 are side, rear and front elevations of a cam follower of the valve according to the invention;

DETAILED DESCRIPTION OF PREFERRED EMBODIMENTS

Figure 1:
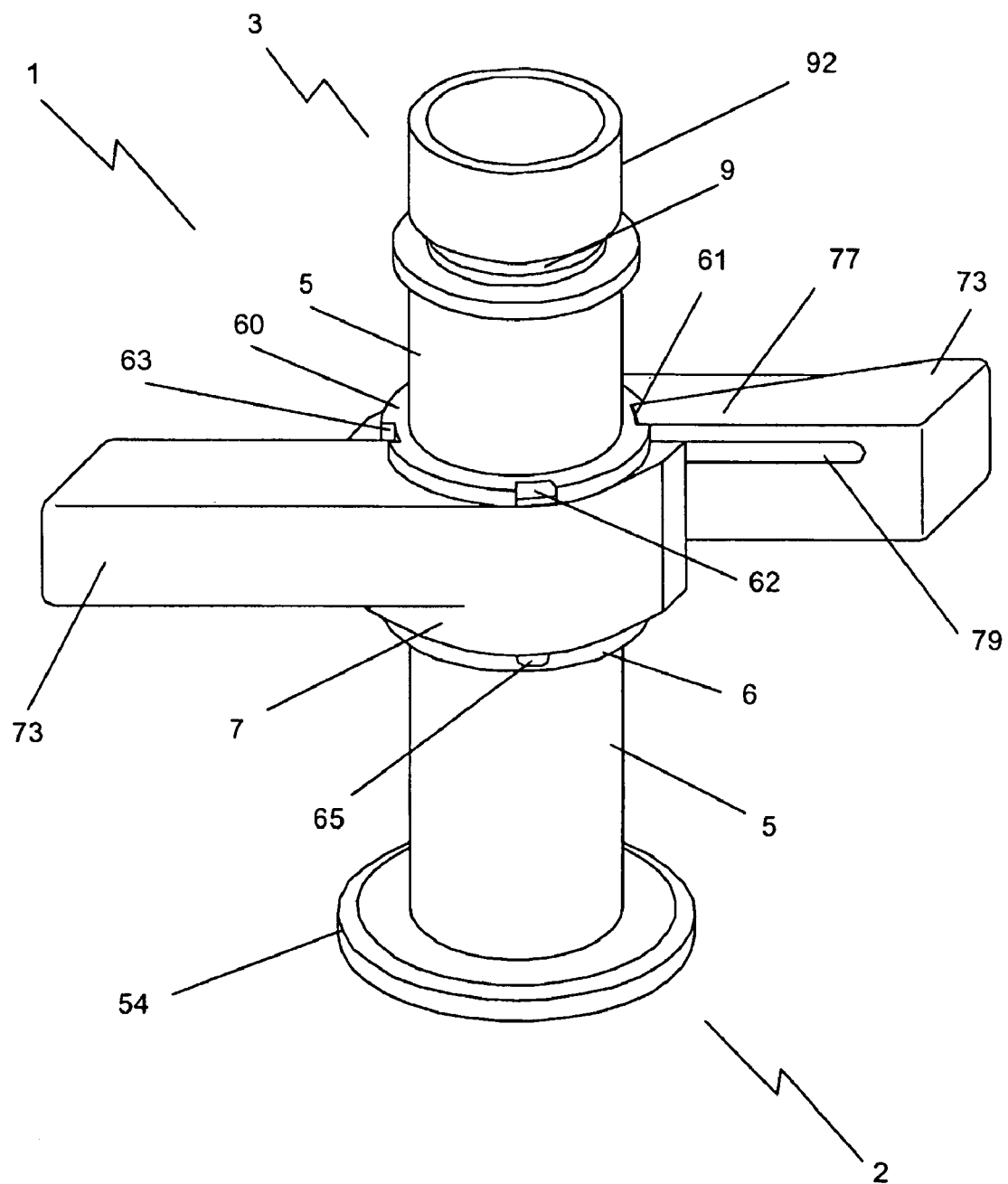
FIG. 1 is a perspective view of a valve according to the invention.
Figure 3:
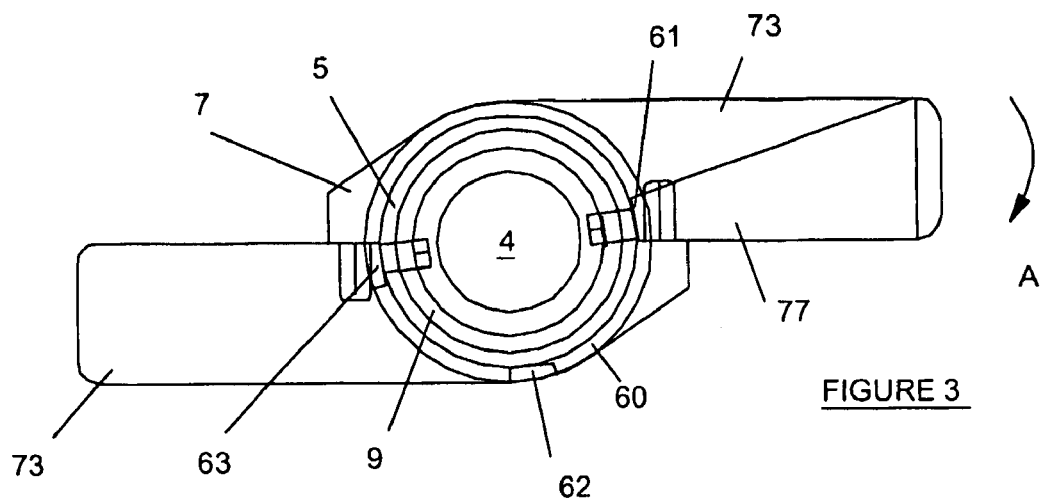
FIG. 3 is a plan view of the valve of FIG. 1.
Figure 2:
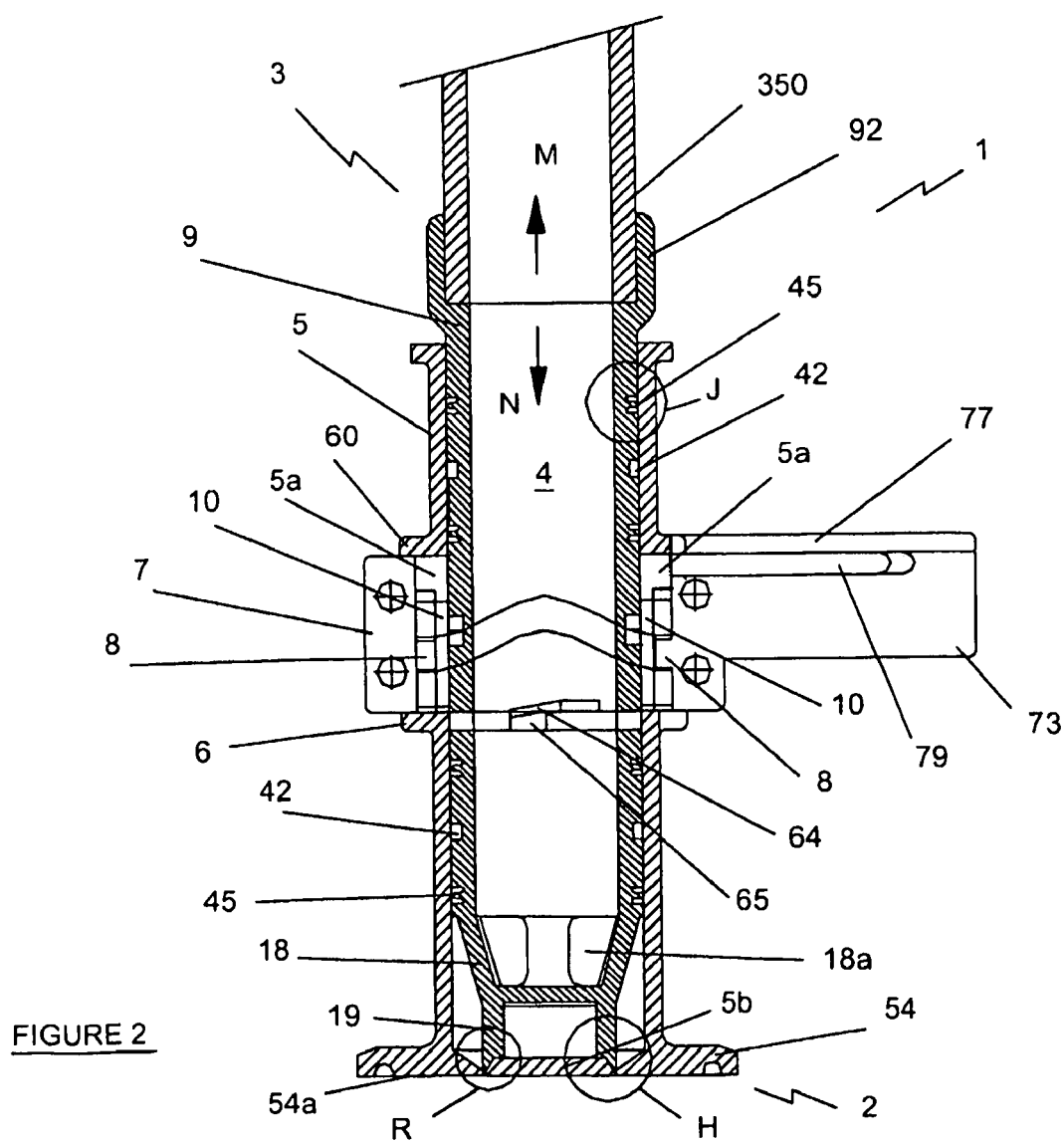
FIG. 2 is a cross-sectional elevation view of the valve of FIG. 1.

Referring to the drawings and initially to FIGS. 1 to 3, there is shown a valve indicated generally by the reference numeral 1. The valve 1 has a body having first and second open ends 2, 3 and a passageway 4 extending between the ends 2, 3.

The body of the valve 1 comprises a hollow tubular housing 5. A hollow tubular piston 9 is disposed within the housing 5. The piston 9 is movable along a longitudinal axis of the housing 5 by an actuator 7 rotatably mounted on the outside of the housing 5 and coupled to the piston 9 via a cam mechanism comprising a cam 8 of the actuator 7 and a pair of cam followers 10 mounted on the exterior of the piston 9. The housing 5, the actuator 7 and the cam mechanism will be described in detail below.

Referring to FIGS. 4 to 7 the housing 5 is provided by a hollow tube having an internal bore 510. First and second parallel spaced apart guide rails 6 and 60 respectively project laterally from the external surface of the housing 5. The first guide rail 6 faces the first end 2 of the valve and the second guide rail 60 faces the second end 3. The guide rails 6, 60 encircle the housing 5 in a plane normal to the longitudinal axis of the housing 5. The actuator 7 is mounted on the portion of the housing 5 defined between the guide rails 6, 60. A pair of diametrically opposing guide slots 5a for receiving the cam followers 10 (see FIG. 2) of the cam mechanism are formed in the side wall of the housing 5 between the exterior and interior of the housing 5 and extends parallel to the longitudinal axis of the housing 5.

At the first end 2 of the valve 1, the housing 5 is connectable to a vessel (not shown) from which fluid is to be transferred through the valve 1. The housing 5 has a flange 54 at the second end 2 of the valve 1, and the base of the flange 54 comprises a mating surface 54a for mating in use with a corresponding mating surface of the vessel. A washer (not shown) may be placed between the mating faces of the valve and the vessel. A groove 54b may be provided in the mating surface 54a for receiving a washer. A matching groove may be formed in the mating surface of the vessel. The flanges of the valve and the vessel and as the case may be, the washer, may be secured together by a suitable fixing means such as a triclover clamp 315 (see FIG. 34).

A seal 5b blocks the opening of the valve 1 at the first end 2. As shown in FIGS. 8 and 8a, the seal 5b is formed continuously with the flange 54 and has an outer surface 5c which, together with the mating surface 54a of the flange 54, forms a sterilisable external surface of the valve 1. In the present embodiment of the valve 1, the seal 5*b* is in a form of a disc. A junction region 5*d* encircles the seal 5*b* and connects the flange 54 and the seal 5*b*. The junction region 5*d* is formed by way of reduction of material thickness between the seal 5*b* and the flange 54 and has a uniform cross-section along its entire length. In the present case, the reduction of material thickness between the seal 5*b* and the flange 54 is made on internal sides of both the seal 5*b* and the flange 54, i.e. the sides which face the second open end 3 of the valve 1. Furthermore, the reduction in thickness is obtained by forming a notch 50 defined by surfaces 5*e* and 5*f* on the interior sides of the seal 5*b* and the flange 54, respectively. The surfaces 5*e* and 5*f* converge towards the opening of the second end 2 so that the junction region 5*d* includes the line of intersection of the converging surfaces 5*e* and 5*f*. The surface 5*e* is bevelled in relation to the longitudinal axis of the housing, whereas the surface 5*f* is substantially parallel to said longitudinal axis. Such a formation of the junction region 5*d* enables quicker and easier separation of the seal 5*b* from the flange 54. Also, the uniformity or the cross section of the junction region 5*d* and the presence of the fracture line reduce risk of the integrity of the valve being compromised during breakage of the junction region 5*d*. When the valve 1 is actuated, the seal 5*b* and the flange 54 separate at the junction region 5*d* to provide a fluid passageway through the valve 1. It will be appreciated that ways to obtain reduction of material thickness between the seal 5*b* and flange 54 may vary in other embodiments of the valve as long as the junction region includes a line of intersection of at least two converging surfaces of the seal and the flange.

The seal 5*b* has a wall or cylinder 5*g* projecting from the internal side of the seal 5*b* for fastening the seal 5*b* to the piston 9. As shown in FIG. 9, the cylinder 5*g* has a series of alternating annular grooves 502 and ribs 501 around its outer cylindrical surface, the purpose of which will be described below. The cylinder 5*g* may be a hollow cylinder, as in the herein described embodiment of the valve, but is not limited to such a configuration. Still referring to FIGS. 8 and 8*a*, the surface of the side wall which defines the internal bore 510 of the housing 5 comprises a first portion 12 near the opening of the first end 2 which converges towards the first end 2. The wall surface further comprises a second portion 13 proximal the second end 2 which is substantially perpendicular to the longitudinal axis of the housing 5. A third wall surface portion 14 extends from the second portion 13 towards the first open end 2 of the valve 1 and comprises the surface 5*f* of the flange 54 which is substantially parallel to the longitudinal axis of the housing 5. The boundary between the second portion 13 and the third portion 14 defines a sharp rim 15. It will be appreciated that angles of inclination of the wall portions 12, 13 and 14 in relation to the longitudinal axis of the housing 5 may vary in different embodiments of the valve, as long as there is provided an inwardly protruding sharp rim about the opening of the first end 2.

Referring to FIGS. 10 to 12*a*, the piston 9 has a first end 17 which in use is positioned proximal the first end 2 of the valve, a second end 21 proximal the second end 3 of the valve 1 and a bore 9*a* extending between the ends. The bore 9*a* constitutes a part of the fluid passageway 4 of the valve 1. The piston 9 has a funnel portion 18 at the first end 17 which in use converges towards the first end 2 of the valve 1. A skirt 19 extends axially from the narrow end of the funnel portion 18. The skirt 19 defines a cavity 19*a* with an opening facing the first end 2 of the valve 1 in use. The cavity 19*a* has a first section 19*b* proximal the base of the skirt 19 for receiving the cylinder 5*g* of the seal 5*b* and a second section 19*c* proximal the opening of the cavity 19*a* sized and shaped for receiving a body of the seal 5*b*. The interior surface of the cavity 19*a* defining the first section 19*b* has a series of alternating annular ribs 19*d* and grooves 19*e* which match the grooves 502 and the ribs 501 of the cylinder 5*g*. Materials of the cylinder 5 and the portion of the skirt 19 defining the first section 19*b* of the cavity 19*a* are selected such that the ribs 501 and 19*e* are resiliently deformable, e.g. plastics materials.

On assembly of the valve 1, when the piston 9 is inserted into the internal bore 510 of the housing 5, the cylinder 5*g* is received in the first section 19*b* of the skirt cavity 19*a*. As the cylinder 5*g* enters the first section 19*b*, the ribs 501 of the cylinder 5*g* and the ribs 19*e* of the first section 19*b* deform to enable advancement of the cylinder 5*g* towards the base of the skirt 19. When the free end of the cylinder 5*g* reaches the end of the cavity 19*a*, the ribs 501 of the cylinder 5*g* snap into the grooves 19*e* of the first section 19*b*. Likewise, the ribs 19*d* of the first section 19*b* snap into the grooves 502 of the cylinder 5*g*. In this position the seal 5*b* is locked together with the piston 9 (see FIG. 13). Thus, the seal 5*b* is permitted to move only on displacement of the piston 9 to which it is connected.

It will be appreciated that other coupling means may be provided between the seal 5*b* and the piston 9 to enable displacement of the seal within the valve 1.

As shown in FIG. 13*a*, the above described rib/groove arrangement between the seal 5*b* and the skirt 19 may be strengthened by interference-fitting a plug 80 into a corresponding recess 5*h* in the cylinder 5*g*. The interference-fit between the plug 80 and the cylinder 5*g* causes the cylinder 5*g* to expand laterally thus increasing contact forces between its exterior and the skirt 19. The plug 80 is inserted into the recess 5*h* via a through aperture 9*b* in the base of the skirt 19 connecting the cavity 19*a* and the inner bore 9*a* of the piston 9. Resiliently deformable ribs 81 encircle the portion of the plug 80 which seats in the aperture 9*b* to provide an efficient fluid-tight seal between the bore 9*a* and the cavity 19*a*.

The funnel portion 18 of the piston 9 has a plurality of through apertures 18*a* which enable access of fluid into the internal bore 9*a* of the piston 9 upon separation of the seal 5*b* from the flange 54.

The external surface of an end region 190 of the skirt 19 (see FIGS. 12 and 12*a*) has a step portion 191 where the external surface tapers towards the first end 2 of the valve 1. The step portion 191 leads to an end portion 192 which is substantially cylindrical. The end portion 192 is adjacent the open end of the cavity 19. A transitional curved surface area 193 is provided between the step portion 191 and the end portion 192 of the skirt 19. It will be appreciated that angles of inclination of the surfaces of the step portion 191 and the end portion 192 may vary in different embodiments of the valve so long as there is provided a transitional curved surface area therebetween. The purpose of the curved surface area 193 is for engaging the sharp rim 15 of the internal bore 510 of the housing 5 and will be described below. Materials of the region of the housing 5 containing the sharp rim 15 and the end region 190 of the skirt 19 are selected such that the sharp rim 15 and the curved surface area 193 are plastically deformable, e.g. plastics materials. The end region 190 is sized and shaped to occupy the notch 50 in an assembled ready to use state of the valve 1 (see FIG. 2).

The cam 8 is provided in a form of a continuous bent ledge which projects from the inner surface of actuator 7 (see FIG. 2). The cam 8 has a pair of first cam slopes 8*b* which alternate with a pair of second cam slopes 8*c* (see FIGS. 18 to 20). During relative travel of the cam followers 10 along the first cam slopes 8*b* on rotation of the actuator 7, the cam followers 10 ascend the first cam slopes 8*b*, and the piston 9 is displaced and moved away from the first end 2 of the valve 1 in the direction of the arrow M in FIG. 2, i.e. towards the second end 3 of the valve. Thus the seal 5b, which is locked to the piston 9, will be torn off the housing 5 along the junction region 5d until it separates from the flange 54 and withdrawn into the body of the valve 1 with the piston 9.

In order to enable the breakage of the junction region 5d, resistance of the ribs 501 and 19e of the cylinder 5g and the skirt 19, respectively to the displacement force of the piston 9 must be greater then the resistance of the fracture line 5d to said force. Upon rupture of the junction region 5d between the seal 5b and the housing 5 fluid can flow from a vessel connected to the first end 2 of the valve 1 into the internal bore 9a of the piston 9 through the apertures 18a of the funnel portion 18. The fluid exits the valve 1 at the second end 3 and enters a downstream processing manifold.

In many applications, this valve will be used as a single-use valve which is discarded after completion of the fluid transfer. However, the valve 1 is also operable to be re-closed after the seal 5b has been broken away. Re-closure may be required when, for example, after actuation of the valve a leak occurs in the system, or in any other hazardous circumstances or where intermittent operation of the process is required. Another circumstance in which it is desirable to be able to close the valve is where potentially hazardous materials, such as biological materials, are transferred, and it is desirable to close the valve prior to discarding it, to ensure that any hazardous materials within it may not contaminate the outside environment during disposal.

For re-closure, there are provided the second cam slopes 8c. Further rotation of the actuator 7 in the same direction after the junction region 5d has been ruptured and the seal 5b has been withdrawn into the body of the valve 1 causes the cam followers 10 descend the cam slopes 8c, and the piston 9 is thus displaced towards the first end 2 of the valve 1 in the direction of arrow N in FIG. 2. The rib/groove engagement between the seal 5b and the skirt 19 of the piston 9 provides a firm grip enables the seal 5b to be displaced in both directions along the longitudinal axis of the valve 1. As the piston 9 travels towards the opening of the first end 2, the sharp rim 15 of the internal bore 510 of the housing 5 engages the curved surface area 193 of the end region 190 and displaces a portion of the curved surface area 193 in the direction of its travel thus deforming the materials of the sharp rim 15 and the curved surface area 193. The end region 190 occupies the opening of the flange 54 and the end region 192 abuts the third portion 14 of the flange 54. The contact between the sharp rim 15 and the curved surface area 193 is sufficiently close and tight to form a seal therebetween which prevents any further flow of fluid to or from the body of the valve 1. The linear, non-rotational motion of the piston 9 ensures that no tangential stretching of the material of the sharp rim 15 and the curved surface area 193 occurs which could potentially compromise the seal therebetween.

The inner surface of the cavity 19a must not have any apertures leading to the interior of the valve and/or the contact of the exterior of the seal 5b with the wall of the cavity 19a must be fluid-tight to prevent any fluid bypassing the second seal formed between the sharp rim 15 and the curved surface area 193. The seal 5b and the cavity wall can be sealed together by, for example, providing an endless deformable rib (not shown) projecting from the inner surface of the seal 5b which collapses against the cavity wall upon engagement of the seal 5b with the piston 9.

The seal formed between the sharp rim 15 and the curved surface area 193 is suitable to withstand the rigours of the sterilisation process required in this field. It is essential that no deformation of the materials forming the seal occurs during sterilisation, otherwise the integrity of the seal would be compromised.

Figure 33:
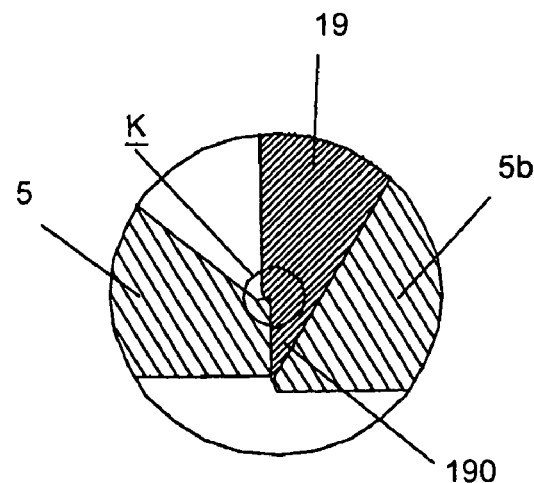
FIG. 33 shows the same. portion of the valve as FIG. 31 but with the opening re-sealed as shown in FIG. 14.

The second cam slope 8c is so shaped that during re-closure, the piston 9 travels towards the opening of the first end 2 of the valve 1 a distance which is greater than the distance travelled by the piston during separation of the seal 5b from the housing 5 so that the free edge of the end region 190 of the skirt 19 projects outwardly from the opening of the first end 2 of the valve 1 upon re-closure (see FIG. 33). This is to enable engagement of the sharp rim 15 with the curved surface area 193 which are axially spaced apart in a ready to use state of the valve 1 when the junction region 5d is intact.

In one application, the valve may only be re-closed once. After re-closure the valve can be disconnected and discarded.

In another application, the re-closed valve can be re-opened by further rotation of the actuator 7 about the housing 5 in the same direction as previous actuations. Such a rotation causes the cam followers 10 to ride over the first cam slopes 8b to move the piston 9 away from the opening of the first end 2 until the sharp rim 15 and the curved surface area 193 disengage thus opening the seal. In order to re-close the valve 1 after it has been re-opened, it is necessary to rotate the actuator 7 further so that the cam followers 10 ride over the second cam slopes 8c until the piston 9 moves into the position in which the sharp rim 15 and the curved surface area 193 are engaged. Thus, multiple actuations of the valve are possible, and in the case of each re-closure, an effective, reliable seal is reformed between the valve and any apparatus to which it is connected.

As shown in FIG. 10, the piston 9 has a sleeve coupling 92 at the second end 21 for coupling with an end 350 (see FIG. 2) of tubing leading to a downstream processing location. Typically, the end 350 of the tubing is welded to the sleeve coupling 92 to create a fluid tight seal between the tubing and the sleeve coupling 92. The tubing may be welded beforehand and supplied with the valve 1.

Figure 17:
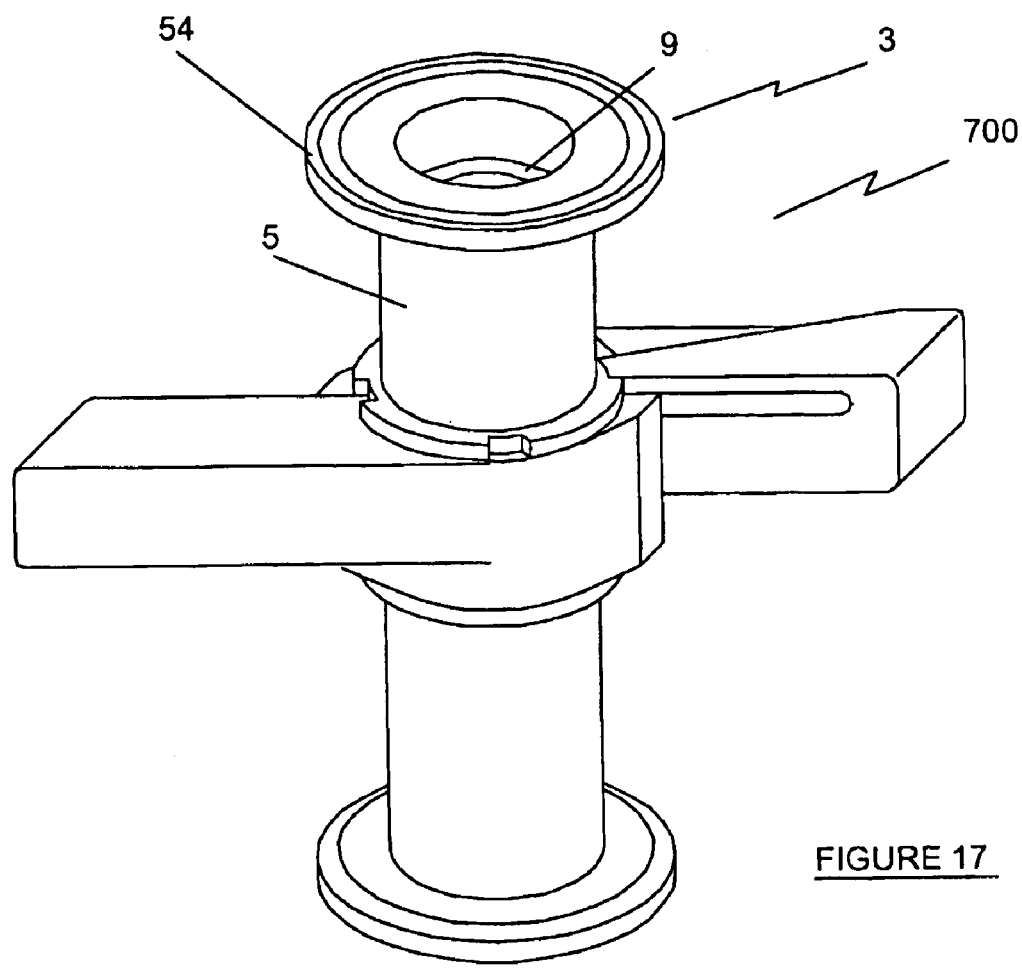
FIG. 17 is a perspective view of a valve having a third modification of the coupling at the second end.
Figure 17A:
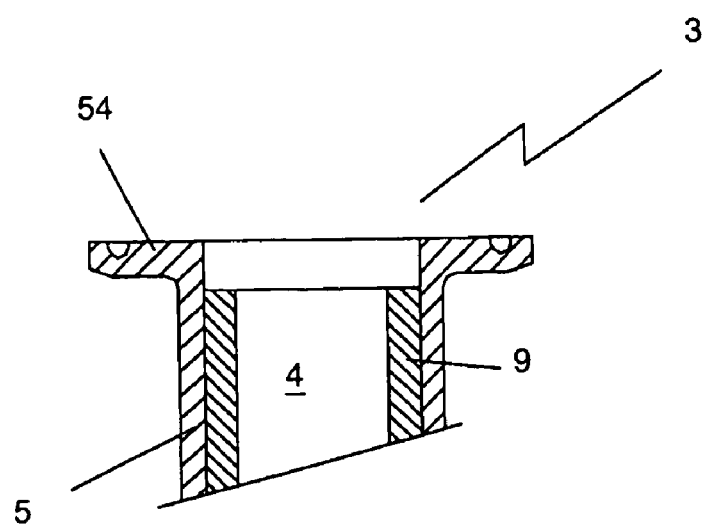
FIG. 17a is a cross-sectional elevation of a portion of the valve of FIG. 17 showing the coupling.

FIGS. 15 to 17a show alternative couplings which may be provided at the second end 3 of the valve 1 for downstream connection of the valve 1. FIGS. 15 and 15a show a barbed fitting 55 extending from the second end 21 of the piston 9 instead of the sleeve coupling 92. The barbed fitting 55 is suitable for connection to various tubes having a range of diameters. FIGS. 16 and 16a show a flange 54 provided at the second end 21 of the piston 9 which is the same as the flange of the housing 5 and is suitable for mating with a mating surface of a downstream coupling device. FIGS. 17 and 17a show a fixed length valve 700, which is identical to the valve 1 except that the housing 5 has a flange 54 identical to the flange of the same number at the first end 2 of the valve 1 by means of which the housing 5 is connected to the downstream processing location. The travel of the piston 9 occurs within the housing 5.

As shown in FIGS. 10 and 10a, a plurality of axially spaced-apart seal members is provided in a form of deformable substantially V-shaped in cross-section ribs 45 formed around the external surface of the piston 9. The external diameter of the piston 9 is smaller than the diameter of the internal bore 510 of the housing 5 whereas the most peripheral region 46 of the surface of each rib 45 projects beyond the external surface of the piston 9 so that the diameter of the most peripheral region 9 is greater than the diameter of the internal bore 510. The portions of the piston 9 containing the ribs 45 are made from a resiliently deformable material, e.g. plastics material and the ribs 45 are formed integrally with the piston 9.

In use, when the piston 9 is loaded into the internal bore 510, the most peripheral region 46 of the rib 45 abuts the wall of the internal bore 510 and deforms in order to permit the piston 9 to enter the bore 510. The abutment is sufficiently close and tight that a seal is formed between the wall and the rib 45 to prevent fluid from flowing between the external surface of the piston 9 and the interior of the housing 5. This seal remains intact during subsequent movements of the piston 9 along the internal bore 510 as the deformable rib 45 drags or "wipes" along the wall of the internal bore 510 (see FIG. 26). As an addition to the ribs 45, an O-ring seal may be placed in one of the two slots 42 formed in the external surface of the piston 9 one at each end of the piston. A modified V-shaped rib 47 (FIGS. 10b and 27) can be used instead of the ribs 45.

A pair of diametrically opposing bores 44 are disposed intermediate the ends 17, 21 of the piston 9. These bores 44 are formed for engagement with spigots 10a extending from the cam followers 10 (see FIGS. 28 and 29).

As shown in FIG. 2, the cam 8 is provided in a form of a ledge of substantially rectangular cross-section projecting proud from the inner surface the actuator 7, i.e. the surface adjacent the housing 5 in use. The cam followers 10 are mounted at diametrically opposing locations on the exterior of the piston 9 by interference-fitting spigots 10a of the cam followers 10 into the bores 44 of the piston 9. The cam followers 10 project proud from the exterior of the piston 9 and extend through the opposing guide slots 5a of the housing 5. Each cam follower 10 has a slot 10b (see FIGS. 28 and 30) formed in an outwardly facing face of the cam follower for receiving the cam 8. Rotation of the actuator 7 about the housing 5 causes the cam 8 to push the cam followers 10 along the guide slots 5a, thus causing the piston 9 to translate linearly about the longitudinal axis of the housing 5 thus displacing the seal 5b. The guide slots 5a also prevent the piston from moving in a side deflection from the linear path during its travel along the longitudinal axis of the housing 5. The linear non-rotational motion of the piston 9 without any side deflection from the straight path provides even load distribution on the junction region 5d during separation of the seal 5b from the flange 54 which increases reliability and safety of valve actuation. Furthermore, such a motion of the piston 9 reduces the risk of compromising the integrity of the valve 1.

As shown in FIGS. 18 to 21, the actuator 7 comprises two component halves 71 and 710, each of which comprises a C-shaped collar 72 having respective pairs of coupling faces 71a, 71b and 710a, 710b. A handle 73 extends laterally from the outer surface of each C-shaped collar 72. In the present embodiment the handles 73 of the component halves 71 and 710 include the coupling faces 71b, 710b, respectively. A pair of connecting pins 74 extend from one of the coupling faces of the C-shaped collar 72 of each component half 71, 710, for example the coupling surfaces 71a, 710a, respectively. The other coupling surface of each component half 71, 710, i.e. the coupling surfaces 71b, 710b, respectively have a matching pair of bores 75 for receiving the connecting pins 74 of the other component half. Aligning the connecting pins 74 of one of the component halves 71, 710 with the bores 75 of the other components half and pressing the two component halves 71, 710 together results in the actuator 7 shown in FIG. 2 in which a central tubular bore (not shown) is defined by the collars 72 of the component halves 71, 710.

When assembling the valve 1, the two component halves 71, 710 are located around the housing 5 between the two guide rails 6, 60 and pressed together until the connecting pins 74 occupy the bores 75. Internal curved surfaces 78 of the C-shaped collars 72 of each component half 71, 710 has a cam half 8a protruding therefrom. Each of the cam halves 8a has the first and second cam slopes 8b and 8c. When the component halves 71, 710 are assembled and pressed together, the cam halves 8a form the cam 8 which continuously encircles the inner surface of the actuator 7. The components halves 71, 710 can be fastened together using various means, for example, screws threaded into corresponding apertures 76, 76a provided in the components halves 71, 710, as shown in FIGS. 22 to 25.

Provision of only one cam half 8a on the inner surface of the actuator 7 is sufficient for the arrangement where only one re-closure of the valve is desired, the valve being in a locked-closed state after re-closure.

As shown in FIG. 30, the slot 10b of each cam follower 10 comprises a pair of opposing convex walls 10c, the shape of which enables point contact between the walls and the cam 8 rather than surface contact thus reducing friction between the cam 8 and the cam followers 10.

Referring to FIGS. 1, 4 to 7 and 18 to 21, a locking mechanism is provided between the actuator 7 and the housing 5 to prevent accidental or spontaneous rotation of the actuator 7. The locking mechanism comprises a tongue 77 formed integrally with or attached to the peripheral end of the handle 73 of one of the component halves 71, 710, for example the component half 71 at one end of the tongue 77. The tongue 77 extends inwardly from the peripheral end of the handle 73. The other end of the tongue 77 is a free end and is engaged with a first recess 61 formed in the guide rail 60 of the housing 5 (see FIG. 2) in an assembled ready to use state of the valve 1, thereby preventing rotation of the actuator 7 about the housing 5. A gap 79 is defined between the tongue 77 and the handle 73 to permit resilient flexing of the tongue 77. In order to release the tongue 77, an external pressure such as a thumb force is applied to tongue 77 to depress it, thereby disengaging the tongue 77 from the first recess 61. The actuator 5 is then free to rotate.

Figure 31:
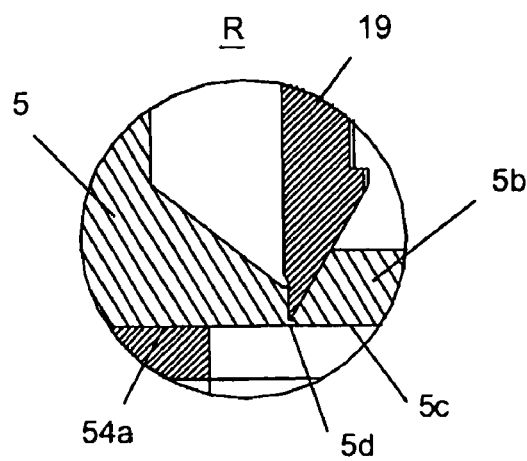
FIG. 31 is an enlarged area R of FIG. 2 showing a seal blocking an opening of the valve in a ready-to-open state of the valve.
Figure 32:
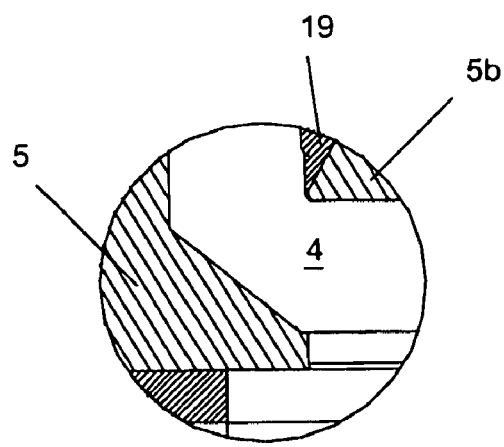
FIG. 32 shows the same portion of the valve as FIG. 31 but with the seal withdrawn into the interior of the valve.

In use, in order to open the valve 1 from a supplied ready-to-open state (see FIGS. 1 and 2), the tongue 77 is released as described above and the actuator 7 is rotated in the direction of arrow A (see FIG. 3 and 31) to a predetermined angle by the handle 73. During the rotation, the first cam slopes 8b push the cam followers 10 in the guide slots 5a towards the second end 3 of the valve 1 thus linearly displacing the piston 9 along the longitudinal axis of the housing. The piston 9 ruptures the junction region 5d and withdraws the seal 5b into the body of the valve 1 (FIG. 32). During rotation of the actuator 7, no external pressure is applied to the tongue 77 as the free end of the tongue 77 passes under the guide rail 6. A second recess 62 (FIG. 2) is provided in the guide rail 6, and the tongue 77 resiliently snaps into the second recess 62 when the actuator 7 reaches a position in which the seal 5b is fully withdrawn into the body of the valve 1 and the valve 1 is open for passage of fluid. In order to re-close the valve 1, the tongue 77 is released from the recess 62 and the actuator 7 is rotated further around the housing 5 to a second predetermined angle while the cam followers 10 travel on the second cam slopes 8c towards the first end 2 of the valve 1 thus displacing the piston 9 so that the sharp rim 15 engages the curved surface area 193, as described above, to re-close and re-seal the valve 1 (see FIG. 33). A third recess 63 (FIG. 3) is provided in the guide rail 6, and the tongue 77 resiliently snaps into the third recess 63 upon re-sealing of the valve 1.

In a modification of the valve in which the valve can only be re-closed once, a second non-releasable lock (not shown) may be built into the valve for preventing any further rotation of the actuator in any direction upon re-closing the valve.

In a modification in which multiple actuations are possible, in order to re-open the valve, the tongue 77 is released from the third recess 63 and the actuator is rotated further about the housing 5. In the presently described arrangement of the valve 1, the rotation of the actuator continues until the tongue 77 firstly passes the first recess 61 and then snaps into the second recess 62. This is the "valve open" position in which the seal 5b in withdrawn into the body of the valve 1 and the sharp rim 15 is disengaged from the curved surface area 193.

A fourth recess (not shown) may be provided in the guide rail 60 diametrically opposite the second recess 62. The tongue 77 thus could snap into the fourth recess on its travel from the third recess 63. In this position, the sharp rim 15 and the curved surface area 193 are disengaged and the seal 5b is withdrawn into the body of the valve 1, just as if the tongue 77 were engaged with the second recess 62. Consequently, this position defines a further "valve open" state".

A third releasable lock may be provided in this modification for manually locking the actuator upon re-closing the valve. Such a releasable lock can be released to enable further actuations, if required.

A resiliently deformable snap-fit stop member 64 (see FIG. 19) is provided on the inner side of the actuator 7, either formed integrally with or attached to the inner side. The stop member 64 prevents reverse rotation of the actuator 7. The stop member 64 projects outwardly from the central bore beyond the rim defining the opening of the actuator 7 which in use faces the first end 2 of the valve 1. Three circumferentially spaced apart pockets 65 (one shown in FIG. 1) are formed in the first guide rail 6 so that the stop member 64 snaps into one of the pockets 65 when the tongue 77 occupies respective recesses 61, 62 or 63. The stop member 64 has a sloping side 64a (FIG. 19a) and a free end 64b. When the actuator 7 is rotated in the correct direction around the housing 5, the sloping side 64a slides against the guide rail 6 thus deflecting the stop-member 64 so that the sloping side is substantially parallel to the rim of the actuator 7 thus allowing the stop member 64 exit a pocket 65. On the other hand, if rotation of the actuator 7 is attempted in the wrong direction, the free end 64b abuts a side wall of a pocket 65 thus preventing rotation of the actuator 7 in that direction. In the modification where the fourth recess is provided for the tongue 77, a respective fourth pocket 65 may be formed in the first guide rail 6.

Provision of only one handle 73 for rotating the actuator 7 about the housing 7 having a locking mechanism is possible for any valve modification.

Figure 34:
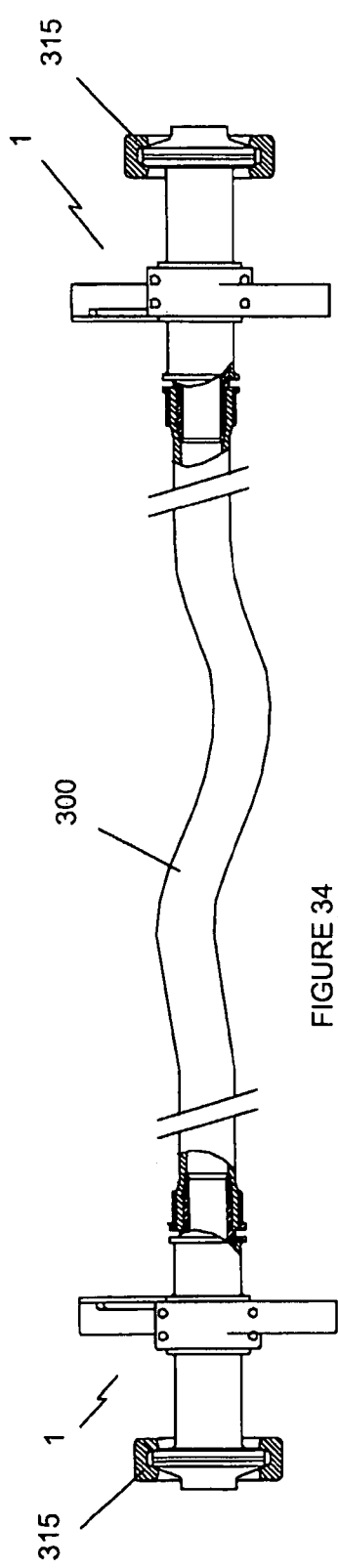
FIG. 34 is a plan view of a fluid transfer assembly comprising two valves according to the invention providing a fluid transfer path between two reservoirs.
Figure 35A:
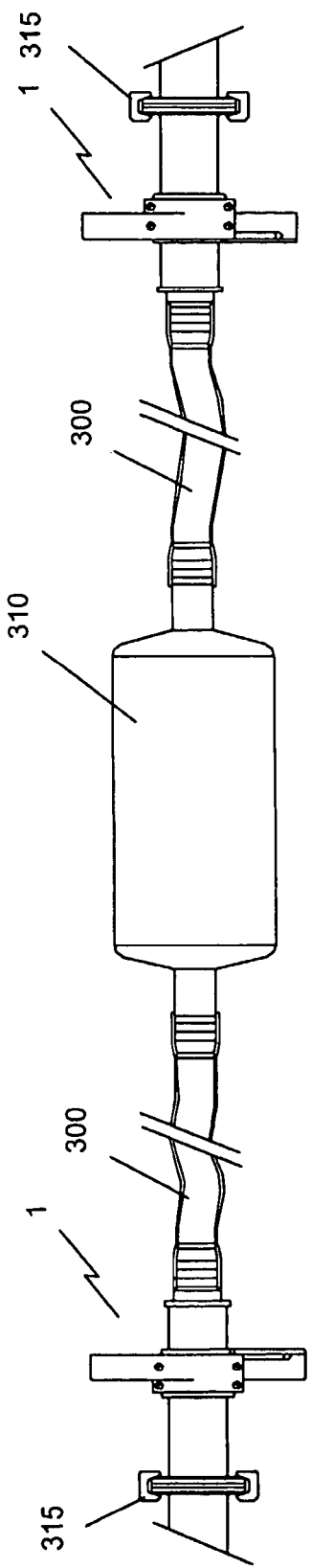
FIGS. 35a and 35b are schematic illustrations of a fluid transfer assembly similar to that of FIG. 34 but including a filter.
Figure 35B:
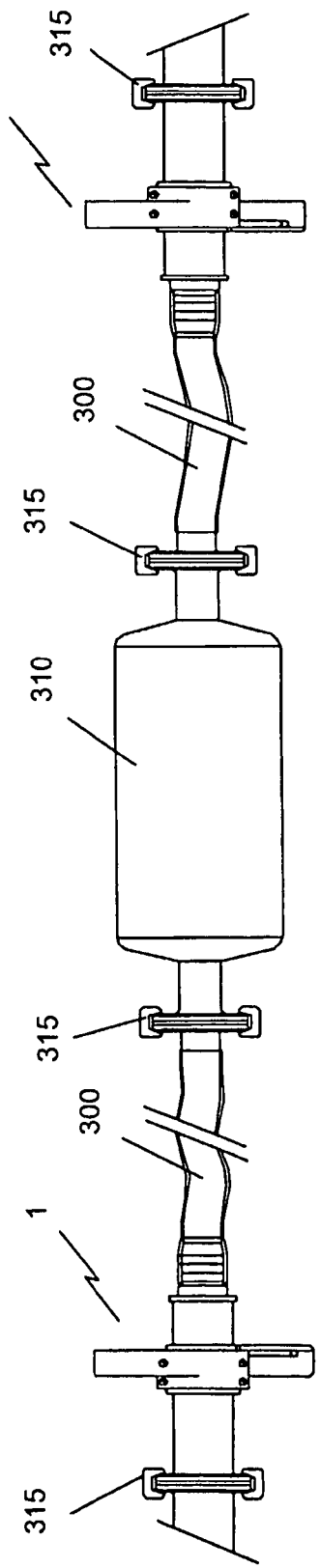

One example of how the valve of the invention may be used in practice will now be described with reference to FIG. 34. In this example, a first vessel is to be connected to a second vessel by means of a tube 300. The tube 300 is provided with a valve 1 at each of its ends. The tube 300 with the valves 1 attached at either end is placed in a bag and the contents of the bag is sterilised, for example by steam, gas, radiation or any other suitable means. In a further step, the bag is opened and one of the valves 1 is removed, thereby exposing the external sealing surface of the valve to environmental contamination whilst the other valve may remain in the bag, although it will inevitably become exposed on opening of the bag. Once released from the bag, valve 1 is coupled to the first vessel and the first vessel is then steam sterilised, thereby also resterilising the exposed face of the valve 1. Next, the first vessel with the attached valve 1 and the bag containing the remaining part of the tube 300 and the other valve is transferred to the site of the second vessel. There, the valve 1 on the opposite end of the tube 300 is released from the bag and connected to the second vessel in the same manner as described in relation to the first valve and the first vessel. The second vessel and the attached valve are then steam sterilised. Now, both valves may be opened providing a sterile fluid path between the first and second vessels. On completion of fluid transfer, the valves are re-sealed and the interiors of the vessels together with the faces of the valves facing those interiors are sanitised and the valves are disconnected from the vessels. The valves are then discarded. If required, it is possible to re-close and re-open the valves during the fluid transfer.

Figure 36A:
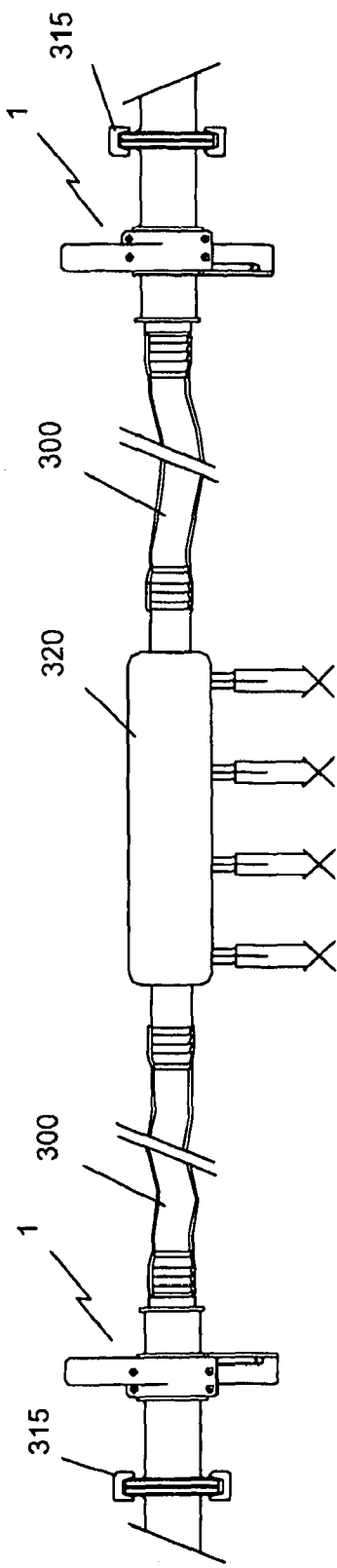
FIGS. 36a and 36b are schematic illustrations of a fluid transfer assembly similar to that of FIG. 34 but including a coupling leading to a test sample manifold.
Figure 36B:
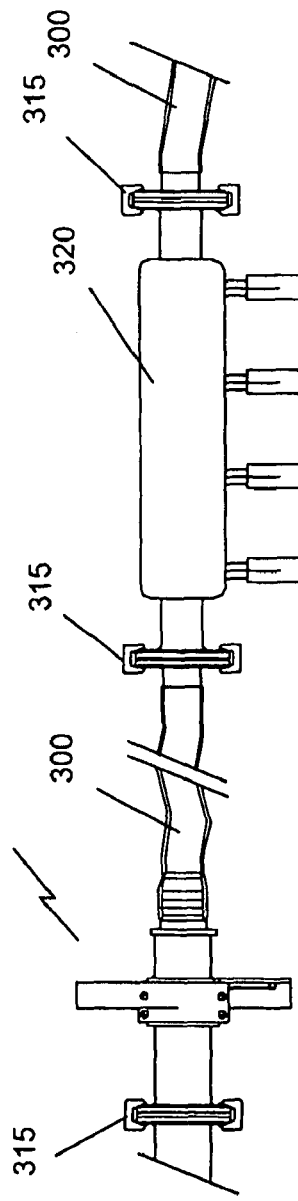

As shown in FIGS. 35a to 36b, the tubing which connects the two valves may include a filter 310 and/or a coupler 320 leading to a test sample manifold. Triclover clamps 315 may be used for connecting the filter 310 and the coupler 320 to the tubing (FIGS. 35b and 36b).

Figure 37:
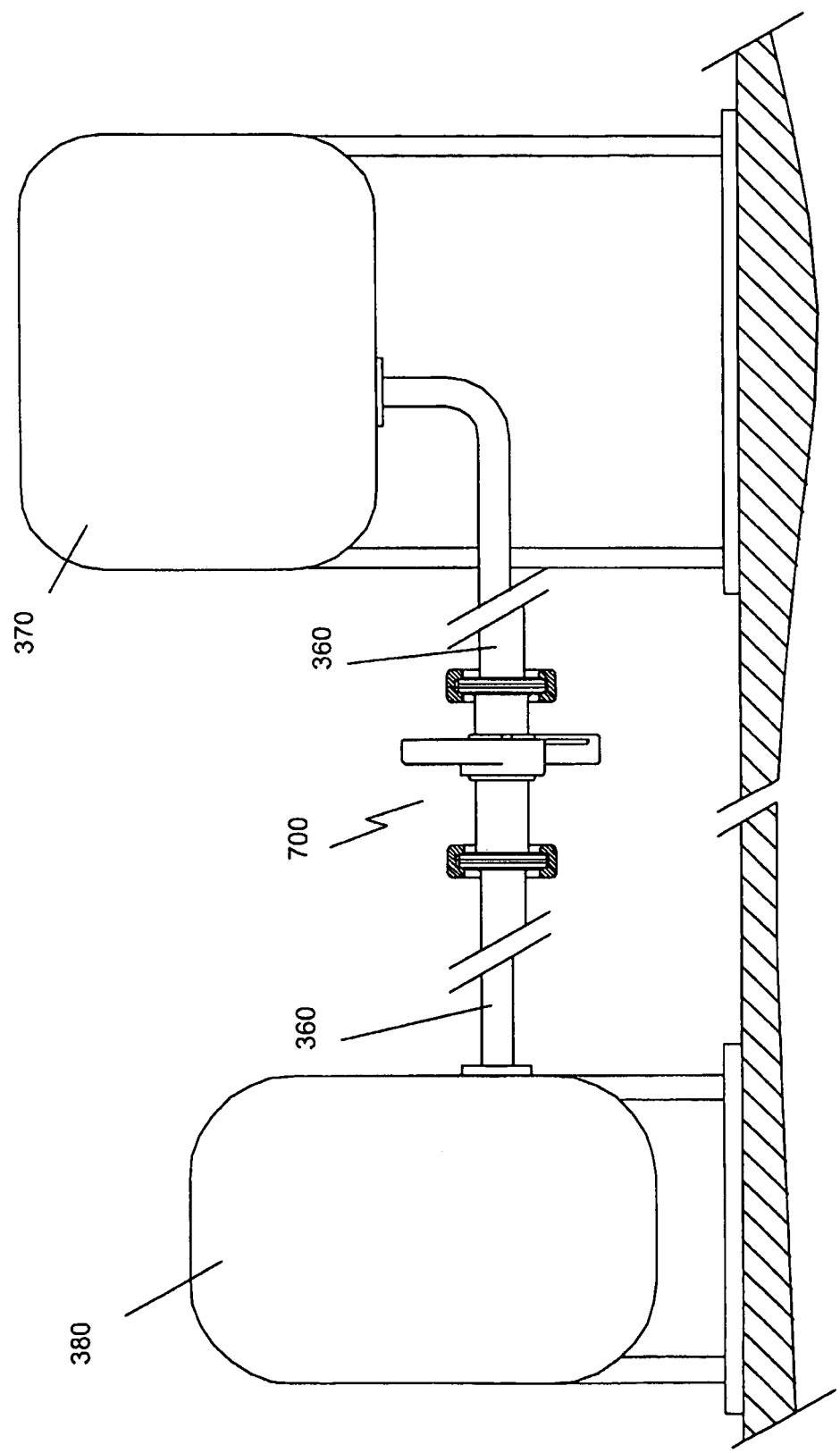
FIG. 37 is a schematic illustration of a valve of FIG. 17 coupled to non-flexible tubing.

FIG. 37 shows a fixed length valve 700 coupled at both ends with rigid pipes 360 which connect vessels 370 and 380.

For operation of the valve of the invention, the valve is pre-sterilised, for example by gas, gamma ray or steam sterilisation, prior to use. At this stage, it is in its closed position. Once sterilised, the valve can be connected to any desired opening of a pipe or vessel. In connecting the valve to the opening, the external surfaces of the valve, including the exterior sealed entry side of the valve, are exposed to the atmosphere, thus sterility of the valve is compromised. Once the valve is connected, the vessel or pipe to which it is attached is sterilised, enabling the external connecting surface of the valve to be resterilised. Once the connecting surface of the valve has been resterilised the valve can be opened when required.

In another embodiment not shown in the drawings, the valve according to the invention may be activated by a sliding actuator. Such a sliding actuator has a pair of opposing parallel side walls each wall having a cam in a form of a ledge projecting inwardly from the wall inner surface and extending along the wall. The actuator is mounted on the housing between a pair of guide rails provided on the exterior of the housing so that the housing is received between the opposing walls and the actuator can be moved laterally perpendicular to the longitudinal axis of the housing. The cams of the actuator are engaged with cam followers similar to those described for the rotary actuator 7 so that sliding motion of the actuator in relation to the housing results in linear longitudinal motion of the piston within the housing.

Figure 38:
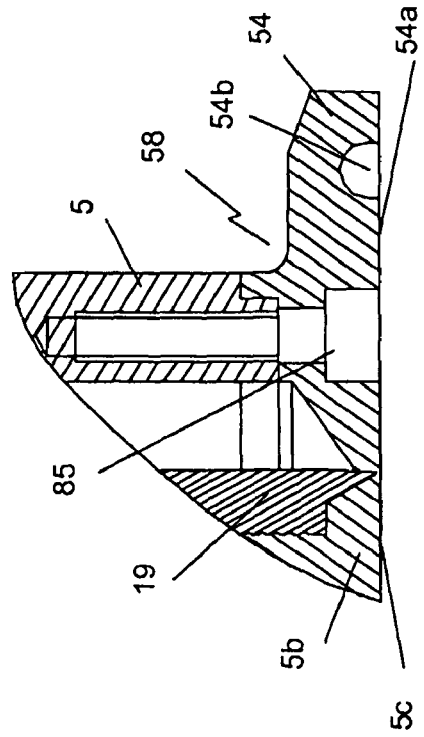
FIG. 38 is a partial cross-sectional elevation of a valve according to the invention having a removable portion containing the seal.

In yet another embodiment (see FIG. 38), a portion of the flange 54 surrounding the seal blocking the open end 2 of the valve may be provided as an attachment 58 which includes the seal 5b and the flange 24. The attachment 58 is secured to the housing 5 at the first end 2 of the valve 1 and fixed in place by screws 85. The housing 5 and the attachment 58 are so configured that the contact between the housing and the attachment 58 is fluid-tight. After each use the attachment 58 is removed and the valve is cleaned. A new attachment 58 with an unbroken seal 5b is then placed into the position blocking the open end 2 of the valve 1.

In another modification (not shown) an attachment may be formed and shaped to provide a secondary function of acting as a sealing washer between the valve and vessel to which it is coupled when the valve and vessel are secured together. A seal such as the seal 5b is formed integrally with the washer, and when the washer is placed between the vessel and the valve, the seal blocks the open end of the valve. The seal of the washer is coupled with the piston of the valve so that on movement of the piston within the valve the seal is separated from the washer to open the valve. In valve arrangements where an attachable seal is used, the housing of the valve can be made from hard materials such as stainless steel or ceramics which can withstand multiple sterilisations.

Figure 39:
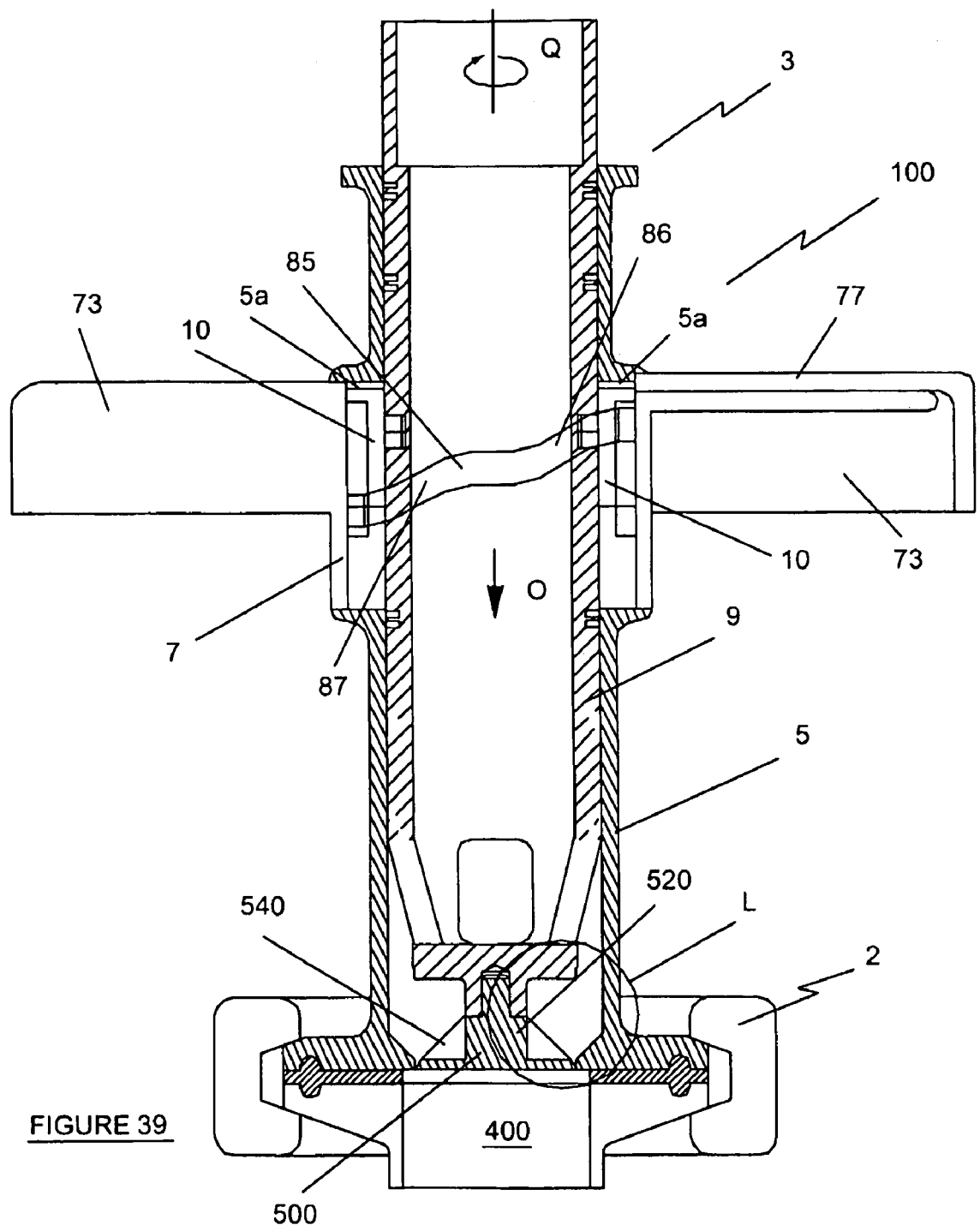
FIG. 39 is a cross-sectional elevation view of a second embodiment of a valve according to the invention.
Figure 40:
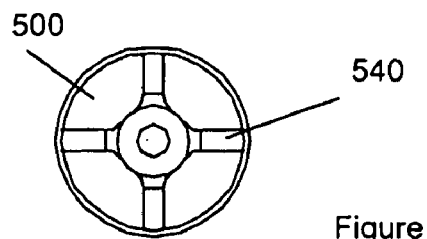
FIG. 40 is a plan view of the seal which blocks an open end of the valve of FIG. 39 in a ready-to-open state of the valve.
Figure 41:
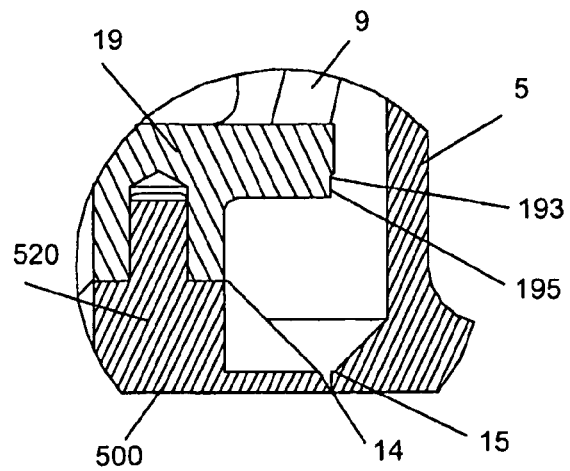
FIG. 41 is an enlarged area L of FIG. 39 showing the seal in the ready-to-open state of the valve.

FIGS. 39 to 40 show a further embodiment of the valve in accordance with the invention and the valve is indicated generally by reference numeral 100. Elements of the valve 100 which are the same as the elements of the valve 1 are indicated by the same numerals in the valve 100. A seal 500 blocks the opening of the valve 100 at the first end 2 thereof. The seal 500 is similar to the seal 5b but has reinforcing ribs 540 extending between the inner face of the seal 500 and an upstanding portion 520 on the inner face. In FIGS. 39 to 43, coupling between the upstanding portion 520 and the piston 9 is illustrated only schematically. In fact, the seal 500 and the piston 9 are coupled together via a rib/groove arrangement similar to that of the valve 1 with or without a plug 80. The valve 100 differs from the valve 1 in that the cam mechanism between the actuator 7, the housing 5 and the piston 9 is arranged to displace the seal 500 outwardly into a passageway of a separate vessel to which the valve 100 is connected at its first end 2 i.e. in the direction of arrow O in FIG. 39 instead of withdrawing it into the interior of the valve 100. Subsequent re-closure of the valve 100 is carried out by pushing the piston 9 further out of the housing 5 in the same direction as during the displacement of the seal 500 in order to engage the sharp rim 15 and the curved surface area 193 as described above.

Figure 44:
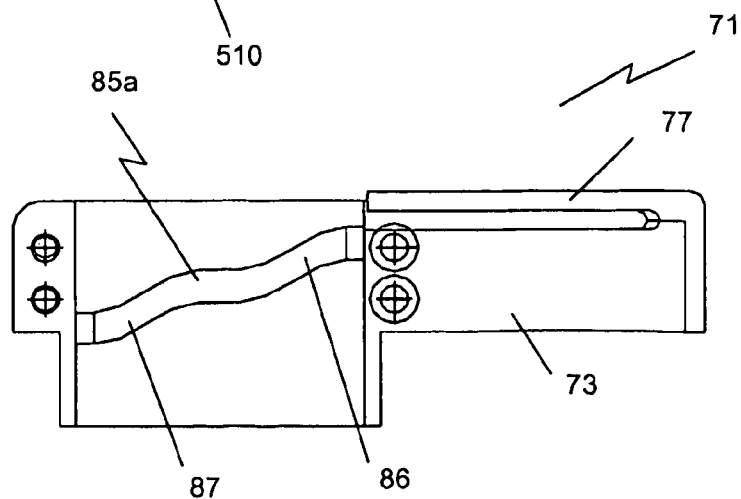
FIG. 44 is an elevation of one component half of a rotary actuator of the valve of FIG. 39.

A continuous cam 85 encircles the inner surface of the actuator 7. The cam 85 is assembled from two cam halves 85a (FIG. 44). Each cam half 85a extends diagonally across the inner surface of its respective component half of the actuator 7 (FIG. 40 shows the component half 71 which has the tongue 77) and has a first step portion 86 and a second step portion 87.

Figure 42:
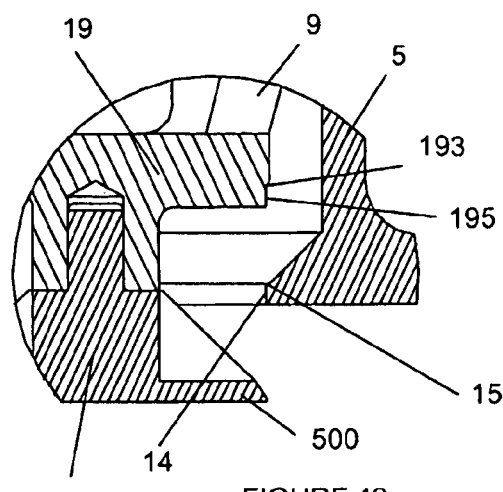
FIG. 42 shows the same portion of the valve as FIG. 40 but with the seal stamped outwardly from its position blocking the opening of the valve.

In use, in order to open the valve 100 from a supplied ready-to-open state (FIGS. 39 and 41), the tongue 77 is released as described above and the actuator 7 is rotated in the direction of arrow Q in FIG. 40 to a predetermined angle by the handle 73. During the rotation, the first step portions 86 push the cam followers 10 in the guide slots 5a towards the first end 2 of the valve 100 thus linearly displacing the piston 9 along the longitudinal axis of the housing 5. The piston 9 ruptures the junction region 5d (FIG. 41) and stamps the seal 5b into a passageway 400 of a separate vessel (FIGS. 39 and 42). In order to re-close the valve 100, the actuator 7 is rotated further around the housing 5 to a second predetermined angle while the second step portions 87 push the cam followers 10 further outwardly thus displacing the piston 9 so that the sharp rim 15 engages the curved surface area 193, as described above, to re-close and re-seal the valve 100 (see FIG. 43).

Figure 43:
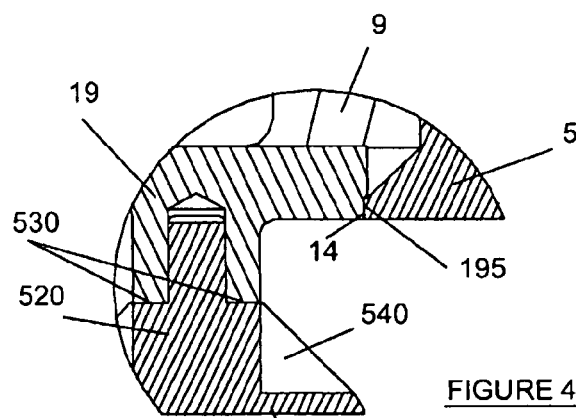
FIG. 43 shows the same portion of the valve as FIG. 40 but with the opening re-sealed in a manner similar to that shown in FIG. 14.

The wall surface portion 14 of the housing 5 and a surface portion 195 of the skirt 19 are substantially parallel and when the sharp rim 15 engages the curved surface area 193, the skirt 19 occupies the opening of the first end 2 of the housing 5 and the surface portion 195 abuts the wall surface portion 14 (FIG. 43).

During rupture of the junction region 5d, the displacement force of the piston is concentrated on shoulders 530 of the seal. Therefore the rib/groove arrangement is subjected to a lesser load than the same rib/groove arrangement in the above described valve 1 where the seal 5b is withdrawn into the valve body. The reinforcing ribs 540 help to reduce the risk of damaging the seal 500 during the rupture.

Figure 45:
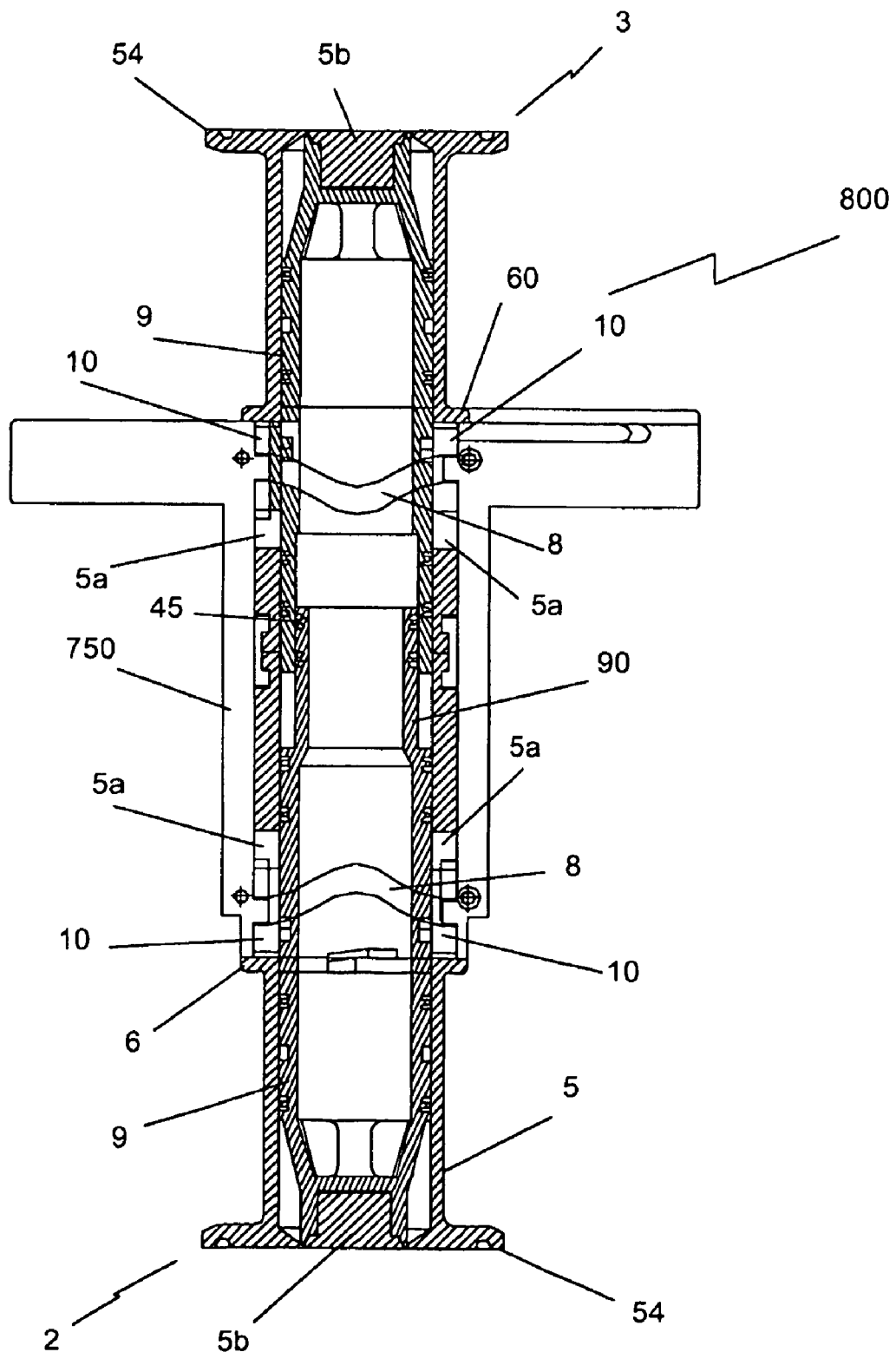
FIG. 45 is a cross-sectional elevation of an embodiment of the valve having seals at both ends of the valve.

FIG. 45 shows a further embodiment of a valve in accordance with the invention indicated generally by reference numeral 800. Elements of the valve 800 which are the same as the elements of the valve 1 are indicated by the same numerals. Valve 800 is a "double-ended" valve, being provided at each of its ends with the seals described above in relation to the valve 1. A flange 54 is formed at each of the first end 2 and the second end 3 of the valve 800. The valve 800 has a pair of first seals 5b closing the openings of the flanges 54 at the first and second ends 2, 3 of the valve in a ready to use state of the valve. Each seal 5b is connected to one of a pair of pistons 9 axially spaced apart within the common housing 5 via an above described rib/groove arrangement. Both pistons 9 have curved surface areas and the flanges have sharp rims like those described above with reference to the valve 1. A common actuator 750 is mounted about the housing 5 between the guide rails 6 and 60. Actuator 570 is similar to the actuator 7 of valve 1 but has a pair of cams 8 formed on its inner surface, the cams 8 being axially spaced apart from each other. Each cam 8 is engaged with a pair of cam followers 10 of one of the pistons 9. The cam followers 10 are movable in their respective guide slots 5a of the housing 5. Rotation of the common actuator 750 in a first actuation causes the cam followers 10 to travel on the cams 8 and move the pistons 9 inwardly from the openings of the flanges 54 thus rupturing the seals 5b and withdrawing them into the housing 5 and opening both ends 2 and 3 of the valve for passage of fluid. Further rotation of the actuator 750 about the housing 5 in a second subsequent actuation causes the pistons 9 to move in a reverse direction towards the ends 2 and 3 thus engaging the sharp rims and the curved surface areas in the manner described above with reference to the valve 1, thereby re-sealing the valve 800. One of the pistons 9 has a tubular extension member 90 at its inwardly facing end. The extension member 90 is slidably engaged with the other piston 9 and in use directs the fluid which flows between the ends 2 and 3. Seals 45 are formed on the extension member 90 to seal between the extension member and the inner surface of the other piston 9 in the same manner as described above with reference to the valve 1. If desired, the valve 800 can be re-opened and re-closed again as many times as required.

It will be appreciated that a valve such as the valve 800 can be modified to have outwardly stamped seals such the seals 500 of the valve 700. It will further be appreciated that a "double-ended" valve may be alternatively provided by taking two valves such as the valve 1 and assembling then together at their respective ends by a suitable coupling means or clamp. Such a valve would have an actuator for each of the individual valves of the assembly so that each end of the assembled double-ended valve could be actuated independently of the other.

The seals 5b and 500 are formed from an appropriate plastics material such as polypropylene and may be coated with a non-stick material such as Teflon™. The material of the seal 5b is not limited to plastics materials and any suitable material known to a person skilled in the art can be used. Ideally the material selected will have received approval for use in the pharmaceutical or biotechnological industries from an appropriate regulatory authority. Plastics, rubber, metal, foil and other seals, whether flexible and/or stretchable or not, are all contemplated to be useful within the scope of the invention.

It will also be appreciated that the above-described cam mechanism is not limited to the configuration comprising a cam formed on the inner surface of the actuator and cam followers engaged with the valve piston. Indeed, many modifications of the cam mechanism are possible as long as it provides linear non-rotational motion of the piston along its own longitudinal axis and the longitudinal axis of the housing. One possible modification may include provision of a curved cam slot formed in the actuator wall and cam followers either formed integrally with the piston or fastened to the outer surface thereof, the cam followers being received in the slot to enable linear translation of the piston in the housing. Other possible ways, not limited to cam pairs, exist for coupling the actuator, the housing and the piston to enable linear longitudinal motion of the piston inside the housing. As described above, the two seal types of the valve, namely the tearable seal 5b and the "contact" seal, are described as being actuated by the same cam mechanism, but it will be understood that the actuation of the different seals may be decoupled.

The valve or any of its parts may be fabricated from any suitable material including heat resistant plastics materials and metals or ceramics. Plastics are particularly preferred for the single use valve.

It will of course be understood that the invention is not limited to the specific details as herein described, which are given by way of example only, and that various alterations and modifications may be made without departing from the scope of the invention as defined in the appended claims.

What is claimed is:

1. A valve comprising a body having first and second open ends and a passageway for fluid between the ends, the first end including a coupling means for sealingly connecting the body about an opening of an external device and a first seal formed with the coupling means closing the open area of the first end, which in use is placeable in register with the opening of the external device, the valve further including a seal displacement means movable within the body so as to displace the first seal permitting fluid to pass along the passageway between the ends, the coupling means and the first seal presenting an external sterilisable mating surface for sealingly mating with a mating surface about the opening in the external device, and an actuation means for moving the displacement means in a first actuation between a ready state in which the first seal is intact and the valve is closed and an open state in which the first seal is separated from the coupling means and moved with the displacement means away from the mating surface so that the valve is open for passage of fluid, the actuation means being engaged with the displacement means via a connecting means and with the body, the connecting means enabling the displacement means to move linearly and non-rotationally along a straight path within the body without side deflection from said straight path;

and wherein the displacement means includes a first plastically deformable portion encircling an outer surface of a member of the displacement means and the coupling means includes a second plastically deformable portion encircling its open area which becomes exposed when the first seal is separated therefrom, the displacement means being movable in a second subsequent actuation to bring the first and second plastically deformable portions into engagement so as to form a second seal between said first and second portions, the displacement means comprising a face continuous with the first portion so that the second seal and the face close the fluid passage.

2. A valve as claimed in claim 1, wherein a mutually engageable gripping means is provided on the first seal and on the displacement means enabling the displacement means to move the first seal away from the mating surface by stamping the first seal outwardly or withdrawing the first seal into the body of the valve.

3. A valve as claimed in claim 2, wherein the gripping means comprise a snap-fit arrangement between the first seal and the seal displacement means comprising first and second snap-fit members provided on the first seal and the seal displacement means, respectively.

4. A valve as claimed in claim 3, wherein the first snap-fit member comprises a wall upstanding from the inner facing side of the first seal, the wall having a series of alternating ribs and grooves encircling an outer surface thereof, and the second snap-fit member is provided in a recess formed in a portion of the displacement means proximal the first seal in use, the recess being configured for receiving the wall, the surface of the portion of the displacement means which defines the recess comprising a series of alternating ribs and grooves which match those of the wall and encircle said surface, so that on assembly of the valve, when the wall is received in the recess, the ribs of the wall and in the recess first resiliently deform allowing the wall to enter the recess, and then snap into respective grooves of the wall and the recess to couple the first seal with the seal displacement means.

5. A valve as claimed in claim 1, wherein the continuous face comprises a portion of the outer surface of the displacement means facing the opening of the first end of the valve and the outer face of the first seal wherein said portion of the displacement means and the first seal are sealingly coupled together.

6. A valve as claimed in claim 1, wherein the displacement means is engaged with the actuation means via the connecting means so that during third and subsequent alternating actuations the first and second plastically deformable portions alternately separate and engage again in order to re-open or re-close the valve.

7. A valve as claimed in claim 1, wherein the displacement means is engaged with the actuation means via the connection means so that during the first actuation the connection means causes the displacement means to move within the body in a direction towards the second end of the valve, and the first seal is withdrawn into the interior of the body; and during the second subsequent actuation the connection means causes the displacement means to move in the reverse direction towards the first end of the valve to engage the first and the second plastically deformable portions and form the second seal.

8. A valve as claimed in claim 1, wherein the displacement means is engaged with the actuation means via the connection means so that during the first actuation the connection means causes the displacement means to move within the body in a direction towards the first end of the valve, and the first seal is pushed outwardly form the opening of the first end of the valve into a passageway of a separate vessel; and during the second subsequent actuation the connection means causes the displacement means to move further in the same direction to engage the first and the second plastically deformable portions and form the second seal.

9. A valve as claimed in claim 1, wherein the first seal is formed integrally with the coupling means, and an endless weakened junction region is provided between the coupling means and the first seal, said junction region enclosing the seal and said junction region comprising at least one fracture line so that when the displacement means moves on first actuation to open the valve it ruptures the junction region along the at least one fracture line thus separating the first seal from the coupling means and opening the valve for passage of fluid; and wherein the reduction in thickness is obtained by forming a notch between the first seal and the coupling means wherein the notch is defined by a pair of converging surfaces, one of which belongs to the first seal and the other of which belongs to the coupling means; and wherein the line of intersection of said surfaces defines the fracture line of the weakened junction region.

10. A valve as claimed in claim 9, wherein the converging surface of the coupling means is substantially parallel to a longitudinal axis extending between the ends of the valve.

11. A valve as claimed in claim 9, wherein the junction region has a substantially uniform cross-section along the entire length thereof.

12. A valve as claimed in claim 1, wherein in a ready state of the valve, the first and second plastically deformable portions are axially separated along a longitudinal axis of the valve extending between the ends of the valve and the displacement means is engaged with the actuation means via the connecting means so that the distance travelled by the displacement means on the second actuation is sufficient to bring said portions into engagement to form the second seal.

13. A valve as claimed in claim 1, wherein one of the first and the second plastically deformable portions has an endless encircling sharp rim and the other plastically deformable portion has an endless encircling curved surface area so that when the displacement means is moved to close the valve, the sharp rim engages the curved surface area and displaces a portion of the curved surface area thereby deforming the materials of the sharp rim and the curved surface area to form the second seal at the opening of the valve.

14. A valve as claimed in claim 13, wherein the first plastically deformable portion is integrally formed with the member of the displacement means, said member being disposed proximal the first open end of the valve in use and comprising the curved surface area;

and the second plastically deformable portion is integrally formed with the coupling means and comprises the sharp rim.

15. A valve as claimed in Claim 14, wherein the displacement means comprises a piston having an internal bore which defines a portion of the fluid passageway of the valve, the piston having a first end which is open and a second end, the member comprising the curved surface area being provided at the second end of the piston; the piston further comprising one or more apertures provided in a wall of the piston adjacent the second end of the piston so that fluid may pass between the interior of the piston and the first end of the valve via the or each aperture.

16. A valve as claimed in claim 15, wherein the actuation means comprises a hollow actuator body movably mounted on the exterior of the valve body, the actuator body being connected to the piston via a cam pair to translate movement of the actuator in relation to the valve body into movement of the piston within the valve body, said cam pair cooperating with a guide means to enable the linear non-rotational motion of the piston along a straight path in the fluid passageway of the valve body so that no side deflection of the piston occurs during said motion.

17. A valve as claimed in claim 16, wherein the actuator has a cam on the internal surface of the actuator, the cam being engaged with at least one cam follower mounted on the outer surface of the piston, and the guide means comprise at least one elongate through slot formed in the wall of the body and extending substantially parallel to the longitudinal axis of the valve body, the cam follower being movable along the through slot, said slot guiding the cam follower during the relative motion of the actuator about the body to effect displacement of the piston within the housing.

18. A valve as claimed in claim 17, wherein the cam has a first region for moving the first seal away from the position blocking the opening of the valve, a second region for displacing the piston in order to engage the first and second portions to form the second seal.

19. A valve as claimed in claim 18, wherein the valve body and the actuator are cylindrical and the actuator is rotatably mounted on the cylindrical exterior of the body, the cam being endless and encircling the internal surface of the actuator and wherein a return region connects a start end of the first cam region and a terminal end of the second cam region to enable multiple revolutions of the actuator about the housing for repeated re-opening and re-closing of the valve.

20. A valve as claimed in claim 16, wherein the actuation means includes a releasable safety lock means for preventing undesired movement of the seal displacement means and a handle by operation of which a user moves the actuator relative to the body, and the safety lock means comprises a tongue releasably engageable with the body for preventing movement of the actuator, the tongue being releasably engagable with the body upon completion of each actuation.

21. A valve as claimed in claim 16, wherein the valve has a stop means for preventing the actuator from moving in a reverse direction about the body after completion of any actuation.

22. A valve as claimed in claim 16, including a non-releasable lock for blocking the actuator on completion of the second actuation of the valve.

23. A valve as claimed in claim 1, wherein first and second seals close each of the first and second open ends of the body, the second end of the valve including a second coupling means having a first seal formed therewith, each first seal being movable by a separate displacement means axially spaced apart from each other within the body and wherein each displacement means includes a first plastically deformable portion and each coupling means includes a second plastically deformable portion so that both ends of the valve can be opened and/or closed.

24. A valve as claimed in claim 23, wherein each displacement means is connected to a separate actuation means to enable independent opening and closing of the valve ends.

25. A valve as claimed in claim 23, wherein each displacement means is connected to the same actuation means.

26. A valve as claimed in claim 1, including a third seal provided for sealing between the body and the displacement means, the third seal comprising at least one deformable plastics rib formed on the body or on the displacement means for contacting the other of the body or the displacement means and for sealing between them when they are stationary or moving relative to one another.

27. A valve as claimed in claim 26, in which the rib is formed integrally with the body or the displacement means.

28. A valve as claimed in claim 26, in which the rib is sufficiently deformable and flexible so that it drags or wipes along the surface with which it is in contact as the body or the displacement means slide with respect to one another.

29. A valve as claimed in claim 26, in which a plurality of ribs are provided, axially spaced apart from one another along the path of relative movement between the body and the displacement means.

30. A valve as claimed in claim 29, including at least one rib formed intermediate the connecting means and the first end and at least one rib formed between the connecting means and the second end.

31. A process for the sterile transfer of fluid from a first vessel to a second vessel comprising the steps of:
 a) coupling a first valve and a second valve according to claim 1 to respective open ends of a length of a conduit;
 b) placing the conduit with the valves attached in a bag and sterilising the bag and its contents;
 c) opening the bag and removing the valve/conduit assembly thereby exposing the external sealing surfaces of the valves to environmental contamination;
 d) coupling the first valve to a first vessel and sterilising the interior of the first vessel thereby also resterilising the exposed face of the first valve;

e) transferring the first vessel with the attached valve/conduit assembly to the site of a second vessel;
f) coupling the second valve to the second vessel and sterilising the interior of the second vessel thereby also resterilising the exposed face of the second valve; and
g) opening the valves thereby breaking the first seal of each valve and allowing fluid to flow between the first and second vessels;
h) re-closing each valve by deploying the actuating means to close the second seal;
i) sanitising the interiors of the first and second vessels together with the closed faces of the valves facing the vessels; and
j) de-coupling the valves from the vessels and discarding the valve/conduit assembly.

32. A process as claimed in claim 31, including effecting any desired number of closing and opening steps of either valve between steps g) and h).

* * * * *